(12) United States Patent
Rehman et al.

(10) Patent No.: US 12,220,430 B2
(45) Date of Patent: Feb. 11, 2025

(54) METHOD FOR KILLING COLORECTAL CANCER CELLS

(71) Applicant: Imam Abdulrahman Bin Faisal University, Dammam (SA)

(72) Inventors: Suriya Rehman, Dammam (SA); Rabindran Jermy, Dammam (SA)

(73) Assignee: Imam Abdulrahman Bin Faisal University, Dammam (SA)

(*) Notice: Subject to any disclaimer, the term of this patent is extended or adjusted under 35 U.S.C. 154(b) by 0 days.

(21) Appl. No.: 18/301,505

(22) Filed: Apr. 17, 2023

(65) Prior Publication Data

US 2023/0248763 A1 Aug. 10, 2023

Related U.S. Application Data

(62) Division of application No. 17/231,231, filed on Apr. 15, 2021, now abandoned.

(51) Int. Cl.

| | |
|---|---|
| *A61K 36/06* | (2006.01) |
| *A61K 9/51* | (2006.01) |
| *A61K 33/08* | (2006.01) |
| *A61K 33/24* | (2019.01) |
| *A61K 33/38* | (2006.01) |
| *A61K 36/07* | (2006.01) |
| *B82Y 5/00* | (2011.01) |
| *B82Y 40/00* | (2011.01) |

(52) U.S. Cl.
CPC ............... *A61K 33/24* (2013.01); *A61K 9/51* (2013.01); *A61K 9/5192* (2013.01); *A61K 33/08* (2013.01); *A61K 33/38* (2013.01); *A61K 36/06* (2013.01); *A61K 36/07* (2013.01); *B82Y 5/00* (2013.01); *B82Y 40/00* (2013.01)

(58) Field of Classification Search
None
See application file for complete search history.

(56) References Cited

U.S. PATENT DOCUMENTS

| | | |
|---|---|---|
| 9,491,947 B1 | 11/2016 | Awad |
| 9,701,552 B1 | 7/2017 | Ortashi et al. |
| 2007/0031461 A1 | 2/2007 | Tanthapanichakoon |
| 2010/0055199 A1 | 3/2010 | Mansoori |
| 2012/0164062 A1 | 6/2012 | Edwards et al. |
| 2015/0147276 A1* | 5/2015 | Ingber .................. A61K 38/482 424/9.5 |

OTHER PUBLICATIONS

Rehman et al.; "Using Fomitopsis pinicola for bioinspired synthesis of titanium dioxide and silver nanoparticles, targeting biomedical applications," Aug. 2020, RSC; RSC Advances, vol. 10, pp. 32137-32147. (Year: 2020).*

Wang et al.; "Investigating Migration Inhibition and Apoptotic Effects of Fomitopsis pinicola Chloroform Extract on Human Colorectal Cancer SW-480 Cells," Plos One, vol. 9, No. 7, article e101303, pp. 1-13. (Year: 2014).*

Saquib et al.; "Titanium dioxide nanoparticles induced cytotoxicity, oxidative stress and DNA damage in human amnion epithelial (WISH) cells," 2012; Elsevier; Toxicology in Vitro, vol. 26, pp. 351-361. (Year: 2012).*

Rajakumar et al.; "Fungus-mediated biosynthesis and characterization of TiO2 nanoparticles and their activity against pathogenic bacteria," 2012; Elsevier; Spectrochimica Acta Part A, vol. 91, pp. 23-29. (Year: 2012).*

Rehman et al.; "A Wild Fomes fomentarius for Biomediation of One Pot Synthesis of Titanium Oxide and Silver Nanoparticles for Antibacterial and Anticancer Application,"Apr. 17, 2020; MDPI; Biomolecules, vol. 10, article 622, pp. 1-15. (Year: 2020).*

Manzoor-ul-haq, et al., "Isolation and Screening of Mushrooms for Potent Silver Nanoparticles Production from Bandipora District (Jammu and Kashmir) and their characterization", International Journal of Current Microbiology and Applied Sciences, vol. 3, No. 9, 2014, pp. 704-714.

Mehjabeen Ansari, "Biosynthesis of Silver nanoparticles (AgNPs) and sustainable management of Mung bean yellow mosaic virus (MYMV) disease", Botany, Shodhgangotri: Repository of Indian Research, 2019, 18 pages.

Mariana Guilger-Casagrande, et al., "Synthesis of Silver Nanoparticles Mediated by Fungi: A Review", Frontiers in Bioengineering and Biotechnology, vol. 7, Article 287, Oct. 22, 2019, pp. 1-16.

Amin Boroumand Moghaddam, et al., "Nanoparticles Biosynthesized by Fungi and Yeast: A Review of Their Preparation, Properties, and Medical Applications", Molecules, vol. 20, Sep. 11, 2015, pp. 16540-16565.

Ramesh Raliya, et al., "Biosynthesis and characterization of zinc, magnesium and titanium nanoparticles: an eco-friendly approach", International Nano Letters, vol. 4, Article No. 93, Feb. 22, 2014, pp. 1-10.

Suriya Rehman, et al., "Using Fomitopsis pinicola for bioinspired synthesis of titanium dioxide and silver nanoparticles, targeting biomedical applications", RSC Advances, vol. 10, 2020, p. 32137-32147.

Hanaa Ali Hussein, et al., "Biosynthesis, Mechanisms, and Biomedical Applications of Silver Nanoparticles", Functional Bionanomaterials, Chapter 14, 2020, pp. 313-332.

Anirudh Singh, et al., "Green synthesis of metallic nanoparticles as effective alternatives to treat antibiotics resistant bacterial infections: A review", Biotechnology Reports, vol. 25, e00427, 2020, pp. 1-11.

Kanchan Bhardwaj, et al., "*Pleurotus* Macrofungi-Assisted Nanoparticle Synthesis and Its Potential Applications: A Review", Journal of Fungi, vol. 6, No. 4, Dec. 2020, pp. 1-22.

Kannan Badri Narayanan, et al., "Biological synthesis of metal nanoparticles by microbes", Advances in Colloid and Interface Science, vol. 156, Issues 1-2, Apr. 22, 2010, pp. 1-13 (Abstract only).

(Continued)

*Primary Examiner* — Tigabu Kassa
*Assistant Examiner* — Ivan A Greene
(74) *Attorney, Agent, or Firm* — Oblon, McClelland, Maier & Neustadt, L.L.P.

(57) ABSTRACT

Silver and titanium oxide nanoparticles produced with *Fomes fomentarius* or *Fomitopsis pinicola* aqueous extracts and methods for treating bacterial infections or cancer using them.

5 Claims, 25 Drawing Sheets

(56) References Cited

OTHER PUBLICATIONS

Ill-Min Chung, et al., "Plant-Mediated Synthesis of Silver Nanoparticles: Their Characteristic Properties and Therapeutic Applications", Nanoscale Research Letters, vol. 11, Article No. 40, Jan. 28, 2016, pp. 1-14.

Clarence S. Yah, et al., "Nanoparticles as potential new generation broad spectrum antimicrobial agents", Daru Journal of Pharmaceutical Sciences, vol. 23, No. 43, 2015, pp. 1-14.

Suriya Rehman, et al., "A Wild *Fomes fomentarius* for Biomediation of One Pot Synthesis of Titanium Oxide and Silver Nanoparticles for Antibacterial and Anticancer Application", Biomolecules, vol. 10, No. 4, Apr. 17, 2020 pp. 1-15.

Andresa A. Berretta, et al., "Functional Properties of Brazilian Propolis: From Chemical Composition Until the Market", Intech, Superfood and Functional Food—An Overview of Their Processing and Utilization, Chapter 4, 2017, pp. 55-98.

Philip, Daizy; "Green Synthesis of gold and silver nanoparticles using Hibiscus rosa Sinensis," 2010; Elsevier; Physica E, vol. 42, pp. 1417-1424. (Year: 2010).

Rajakumar et al.; "Fungus-mediated biosynthesis and characterization of TiO2 nanoparticles and their activity against pathogenic bacteria," 2012; Elsevier; Spectrochimica Acta Part A: Molecular and Biomolecular Spectroscopy, vol. 91, pp. 23-29. (Year: 2012).

Mandal et al.; "The use of microorganims for the formation of metal nanoparticles and their applications," 2006, Applied microbiology and biotechnology vol. 69, No. 5, pp. 485-492. (Year: 2006).

Kurniawn et al.; "Selective Betalain Impregnation from Red Amaranth Extract onto Titanium Dioxide Nanoparticles," 2019; Proceedings of the 5th International Symposium on Applied Chemistry 2019, AIP Conf. Proc. 2175, 020049-1-020049-7. (Year: 2019).

Tobaldi et al.; "Fully quatative X-ray characterization of Evonik Aeroxide TiO2 P25®," 2014, Elsevier; Materials Letters, vol. 122, pp. 345-347. (Year: 2014).

Blumberg et al.; "0.9% NaCl (Normal Saline)—Perhaps not so nomal after all?" 2018, Els ev i er; Transfusion and Apheresis Science, vol. 57, 127-131. (Year: 2018).

Sinko, Patrick J.; "Martin's Physical Pharmacy and Pharmaceutical Sciences," 5th edition, 2006; Lippincott Williams & Wilkins; pp. 221-222. (Year: 2006).

Arya et al.; "Biogenic titanium nanoparticles (TiO2NPs) from Tricoderma citrinoviride extract: synthesis, characterization and antibacterial activity against extremely drug-resistant Pesudomonas aeruginosa," 2020; Springer; International Nano Letters, vol. 11, pp. 35-42. (Year: 2020).

Behnam et al.; "The application of titanium dioxide (TiO2) nanoparticles in the photo-thermal therapy of melanoma cancer model," 2018; Iranian Journal of Basic Medical Science, vol. 21, No. 11, pp. 1133-1139. (Year: 2018).

\* cited by examiner

Fig. 1A
Fig. 1B
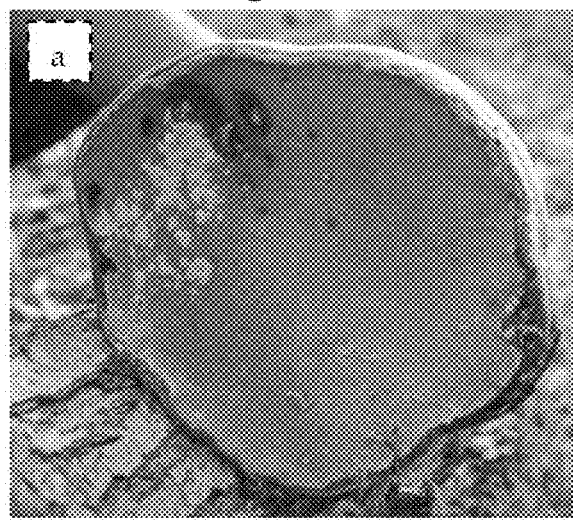
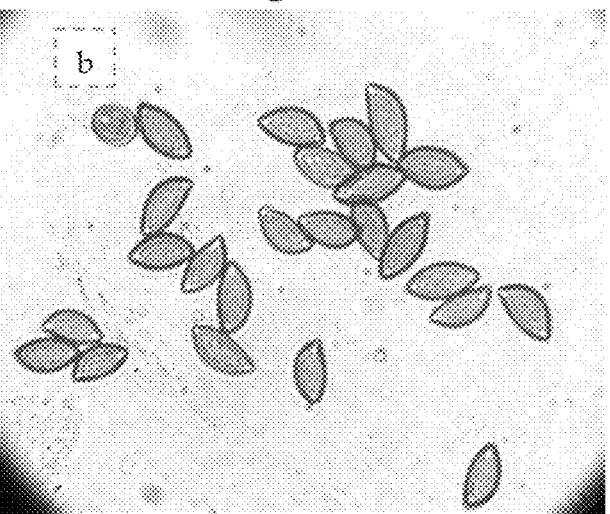
Fig. 2
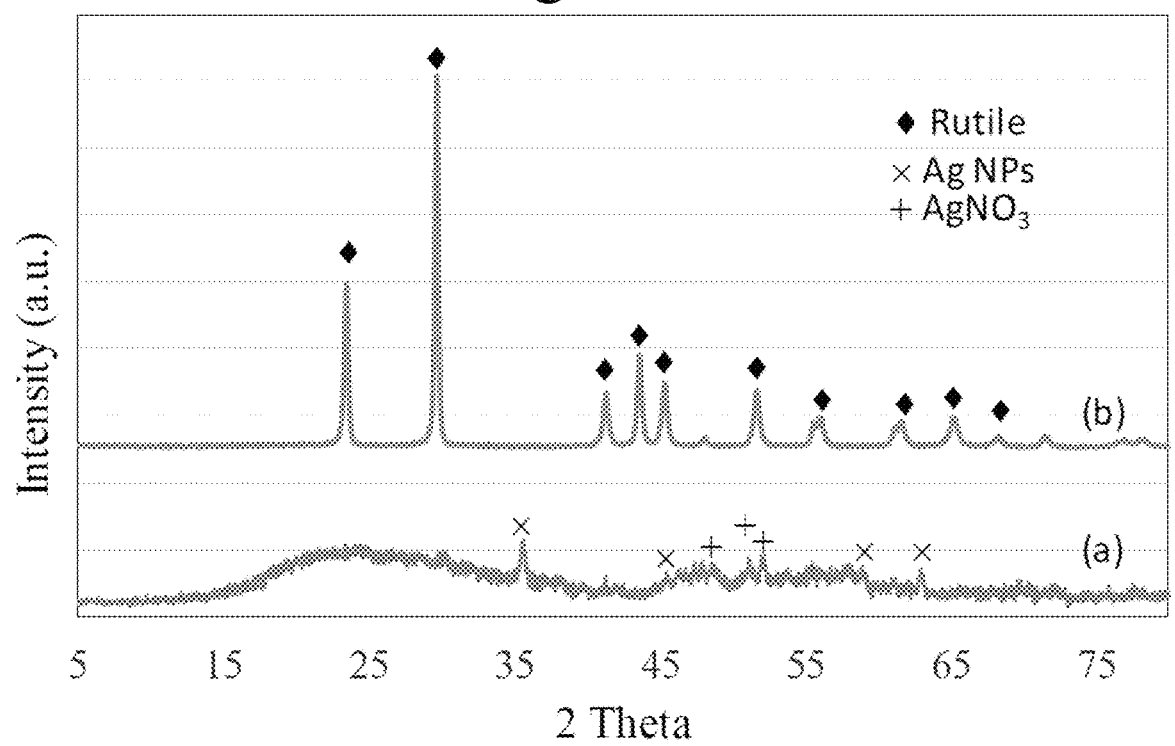

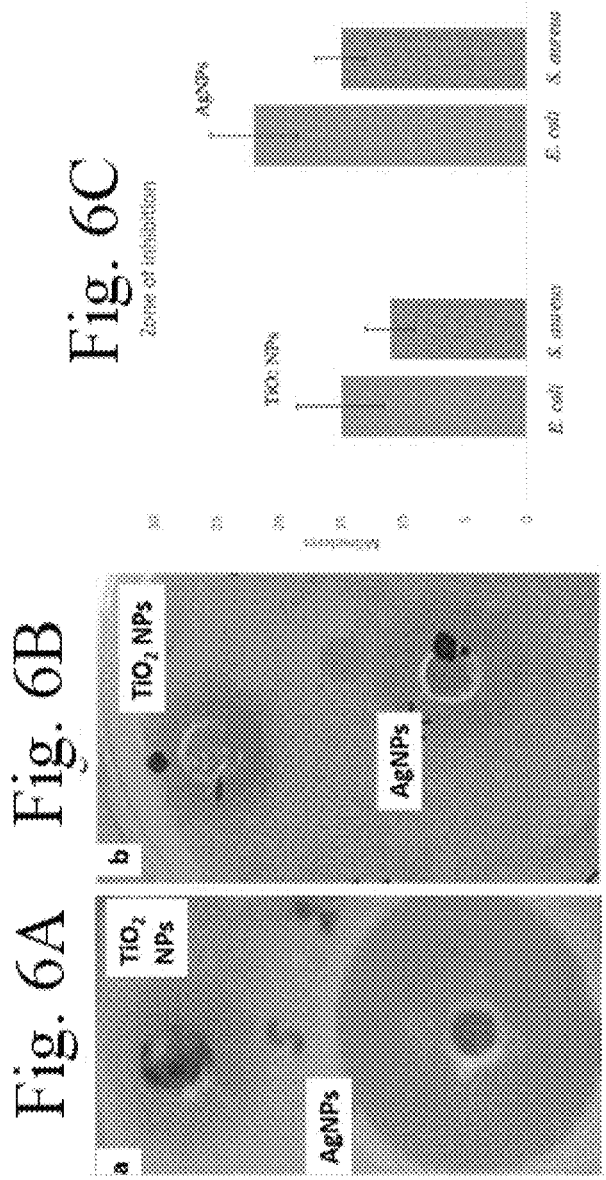

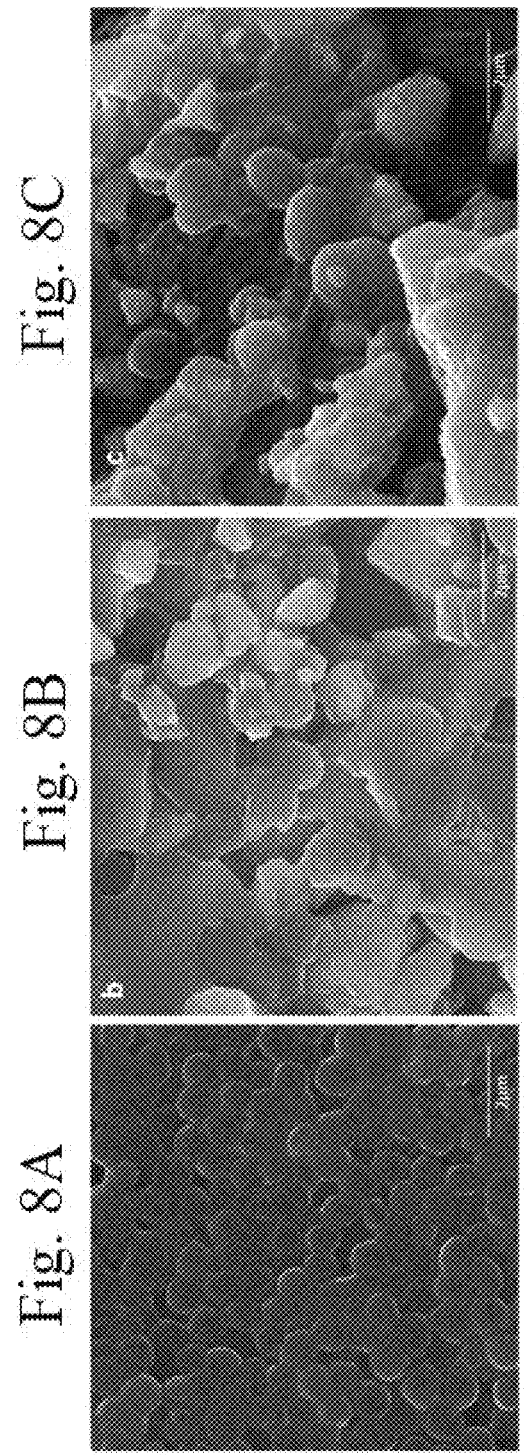

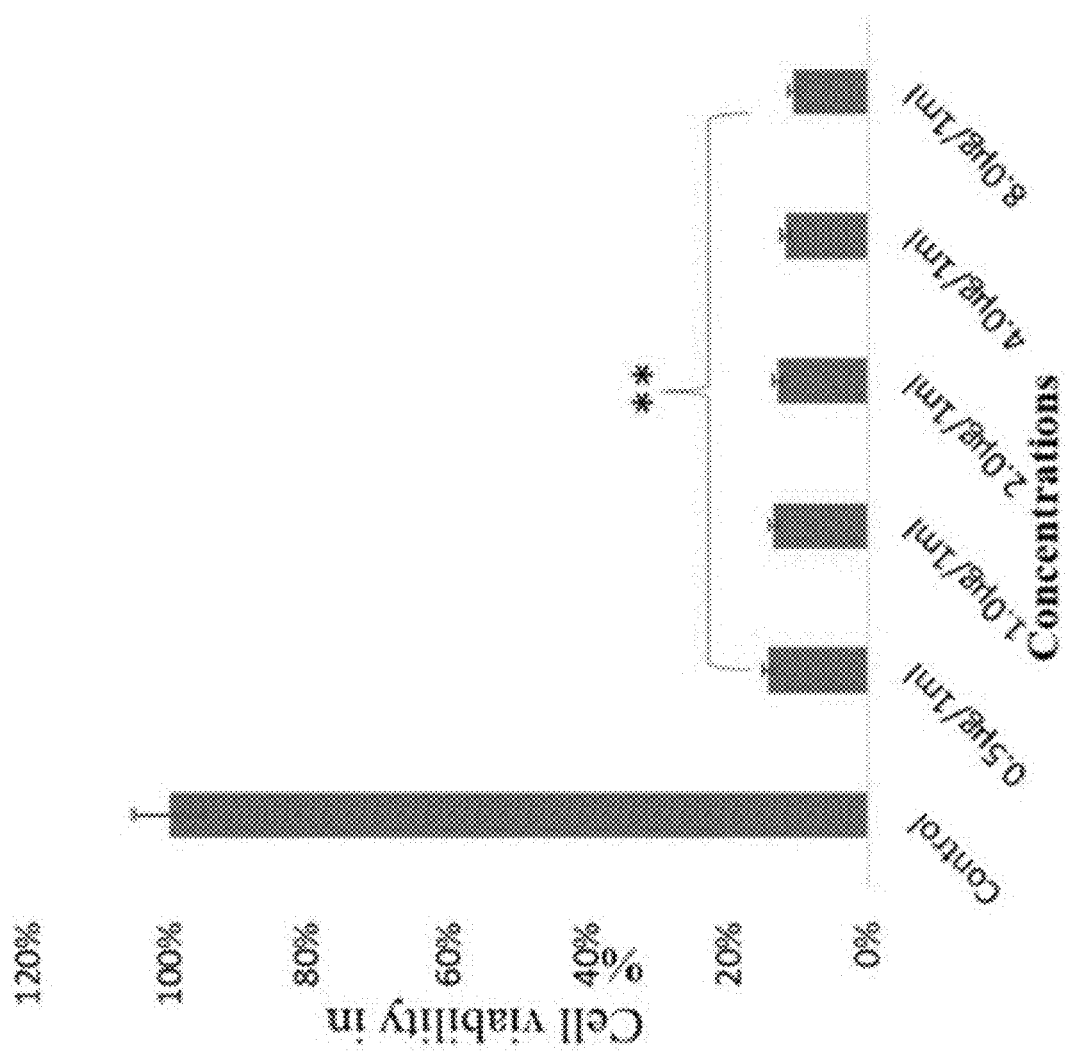

Fig. 20A
Fig. 20B
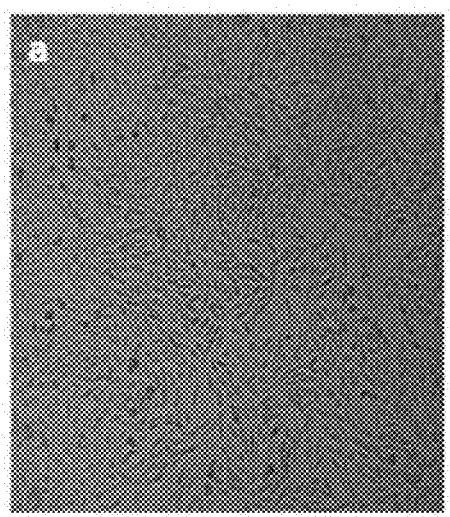
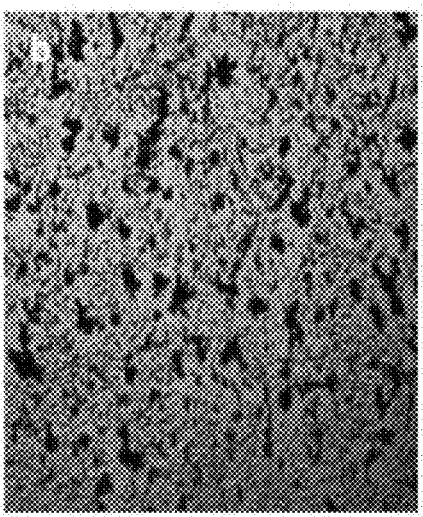
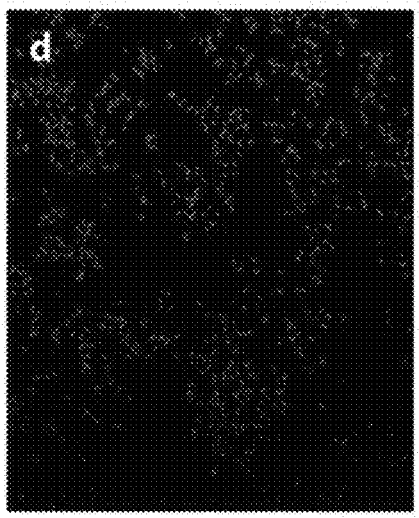
Fig. 20C
Fig. 20D

METHOD FOR KILLING COLORECTAL CANCER CELLS

CROSS-REFERENCE TO RELATED APPLICATIONS

The present application is a Divisional of U.S. application Ser. No. 17/231,231, pending, having a filing date of Apr. 15, 2021.

STATEMENT REGARDING PRIOR DISCLOSURES BY THE INVENTOR OR A JOINT INVENTOR

The following publications disclose related technology: Rehman, S. et al., *A Wild Fomes fomentarius for Biomediation of One Pot Synthesis of Titanium Oxide and Silver Nanoparticles for Antibacterial and Anticancer Application*, Biomolecules, Published: 17 Apr. 2020, 10(4), 622. Rehman, S., et al., *Using Fomitopsis pinicola for bioinspired synthesis of titanium dioxide and silver nanoparticles, targeting biomedical applications*, first published on 28 Aug. 2020, RSCADv., 2020, 10, 32137-32147.

BACKGROUND OF THE INVENTION

Field of the Invention

The disclosure falls within the field of medical nanochemistry. More specifically it pertains to production and use of silver (Ag) and titanium oxide ($TiO_2$) nanoparticles that comprise extracts of certain higher fungi (mushrooms) and use of these nanoparticles to inhibit proliferation and/or viability of bacteria and cancer cells.

Description of Related Art

Nanoparticles (NPs), such as those made from silver, gold, zinc, and titanium, have been used in a variety of different fields including medicine, agriculture, bioremediation, catalysis, electronics and other industries.

Widely used methods for the synthesis of NPs involve the use of a number of chemicals that can detrimentally affect the ecosystem and human health. As a result, efforts have been directed to devising green methods that use organic materials from certain plants instead of harsher or more toxic chemicals. Such methods can provide a more environmental friendly and economical way to synthesize nanoparticles compared to conventional methods using chemicals that are detrimental to humans and animals or to ecosystems. However, the field of green synthesis of nanoparticles is still in its infancy because different plants, fungi and bacteria have different chemical components which affect their abilities to produce useful nanoparticles. Thus, while there is a growing demand for green synthesis of nanoparticles, there is inadequate information about biological sources of materials useful in producing them.

The use of fungi for nanoparticle synthesis, particularly use of the unexplored higher fungi (mushroom), is still in its infancy. The most familiar species of mushrooms belong to the group *Basidiomycota polyporales*, which constitutes an order of about 1800 species of fungi in the division. Polypore, a term used for basidiocarp-producing fungi, appears tough and leathery, typically large (>3 cm), and found mostly on live and dead trees. These basidiomycetes are nonpathogenic, nontoxic and can be grown in pure cultures. However, use of these fungi for biosynthesis of nanoparticles has not been extensively explored and many or most fungi are incapable of reducing metal salts or compounds into nanoparticles having antimicrobial or anti-cancer properties. As disclosed herein the inventors explored methods for biosynthesis of silver (Ag) and titanium oxide ($TiO_2$) nanoparticles using extracts from *Fomes fomentarius* and *Fomitopsis pinicola* and the use of the produced nanoparticles to inhibit Gram-negative and Gram-positive bacteria and cancer cell growth.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

One aspect of the present disclosure is to provide a method for treating a microbial infection or cancer comprising, consisting essentially of, or consisting of administering to a subject in need thereof at least one of *Fomes fomentarius*-$TiO_2$ nanoparticles or *Fomes fomentarius*-Ag nanoparticles in an amount sufficient to inhibit growth or viability of a microorganism or proliferation or viability of cancer.

The Ag and $TiO_2$ nanoparticles disclosed herein contain components of *Fomes formentarius* ("mushroom extract") as shown by FT-IR. This is demonstrated, for example, by the presence of amino and hydroxyl groups in the nanoparticles. Preferably, the nanoparticles disclosed herein substantially conform to the FT-IR spectra described herein. However, in some embodiments, these FT-IR spectra may vary.

In case of AgNPs, the broad peak at about 2940-3290 $cm^{-1}$ indicates the mushroom part from *F. formentarius* of hydroxyl (—OH) and N—H band of primary amines.

A methylene CH stretching peak was observed at 2940 $cm^{-1}$ and a C—O stretching peak was observed at 1655 $cm^{-1}$.

Aromatic and aliphatic amines from mushroom components can be observed at 1406 $cm^{-1}$ and 1000 $cm^{-1}$.

Similarly, for $TiO_2$ NPs, the presence of aliphatic C—N, and aromatic C=N bands corresponding to *F. fomentarius* components were observed.

Preferably, the Ag nanoparticles exhibit a broad peak at about 3290 $cm^{-1}$ corresponding to hydroxyl (—OH) and N—H stretching of primary amine and the $TiO_2$ nanoparticles exhibit by Fourier transform infrared (FT-IR) spectroscopy absorption peaks between 766-1630 $cm^{-1}$, corresponding to Ti—O, aliphatic C—N, and aromatic C=N bands (corresponding to *F. fomentarius*).

In some embodiments *Fomes fomentarius*-Ag nanoparticles comprise fcc crystals

In other embodiments, the $TiO_2$ nanoparticles may comprise $Ti^{4+}$ species corresponding to a tetrahedral coordination.

The AgNPs and $TiO_2$ NPs used in the methods disclosed herein may administer nanoparticles having average diameters or broadest dimensions ranging 5, 10, 20, 30, 40, 50, 60, 70, 80, 90, 100, 110 to 120 nm. Preferably, the particle size of the Ag and $TiO_2$ nanoparticles ranges between 2, 5, 10, 20, 30, 40, 50 to 60 nm. In other preferred embodiments, the Ag nanoparticles range in average diameter or broadest dimension between 10, 20 and 30 nm and the $TiO_2$ nanoparticles between 10 and 80 nm.

The Ag nanoparticles may also comprise at least one of three different types of Ag species: $Ag^+$, $Ag_n^{\delta+}$ and $Ag^0$. While not being bound to a particular theory or explanation, the inventors consider that metallic silver ($Ag^0$) and cationic silver ($Ag^{+)\ may\ attach}$ to the cell membrane leading to disintegration of membrane and induction of apoptotic signaling leading to programmed cell death.

In other embodiments, *Fomes fomentarius*-$TiO_2$ nanoparticles comprise a rutile phase.

In some embodiments, the *Fomes fomentarius*-$TiO_2$ nanoparticles are made using an aqueous extract of *Fomes fomentarius* and titanium isopropoxide. This extract is preferably clarified or filtered to remove solid components. For example, it may be clarified by centrifugation to pellet and remove solid components or may be filtered through a 0.2 or 0.45 μm filter. Preferably, the extract is produced at less than 15, 20, 25, 30, or 35° C. and exhibits reducing activity sufficient to produce nanoparticles. In preferred embodiments, no other reducing agents such as sodium citrate, sodium borohydride, lithium aluminum hydride, sulfur dioxide, thiosulfates, iodides, hydrogen peroxide, hydrazine, diisobutylaluminum hydride, DTT, cyanides are required thus reducing the impact of harmful chemicals on the environment and provided added safety during preparation.

In other embodiments, *Fomes fomentarius*-Ag nanoparticles are made using an aqueous extract of *Fomes fomentarius* and silver nitrate. This extract is preferably clarified or filtered to remove solid components. For example, it may be clarified by centrifugation to pellet and remove solid components or may be filtered through a 0.2 or 0.45 μm filter. Preferably, the extract is produced at less than or equal to 0, 5, 10, 15, 20, 25, 30, or 35° C. and exhibits reducing activity.

This method may be used to prevent, or treat a subject having, a bacterial infection, including but not limited to Gram-negative and Gram-positive infections or to reduce the risk of exposure of a subject to bacteria, for example, by sanitizing skin or medical supplies or instruments. Bacterial infections include but are not limited to those caused by *staphylococcus* such as *Staphylococcus aureus*, by *streptococcus*, such as *Streptococcus pyogenes*, by *Pseudomonas* or by *Corynebacterium*. Skin infections caused by these or other bacteria include cellulitis, erysipelas, bacterial folliculitis, hot tub folliculitis, furuncles, carbuncles, impetigo, erythrasma, and Methicillin-resistant *Staphylococcus aureus* (MRSA) skin infections. Other bacterial infections such as those associated with abrasions, lacerations, punctures, and other wounds, and eye, sinus, respiratory, enteric infections such as food poisoning, STDs (including *chlamydia*, syphilis, gonorrhea) and other internal infections may be treated by bringing bacteria into contact with the *Fomes fomentarius*-Ag or —$TiO_2$ nanoparticles described herein. The above mentioned conditions may also be prophylactically treated or sanitized using compositions containing the Ag or $TiO_2$ nanoparticles disclosed herein.

The *Fomes fomentarius*-Ag and —$TiO_2$ nanoparticle based methods disclosed herein may be used to prevent, or treat a subject having, a neoplasm, tumor, or cancer, including but not limited to colon or colorectal cancer, breast cancer, lung cancer, prostate cancer, melanoma, bladder cancer, kidney cancer, endometrial cancer, leukemia, pancreatic cancer, thyroid cancer, liver or interhepatic bile duct cancer, or brain cancer.

Another aspect of the present disclosure is directed to *Fomes fomentarius*-$TiO_2$ nanoparticles comprising a rutile phase and/or which have an average diameter or broadest dimension ranging from 5, 10, 20, 30, 40, 50, 60, 70, 80, 90, 100, 110 to 120 nm, and/or which exhibit $Ti^{4+}$ coordination.

Another aspect of the present disclosure is directed to *Fomes fomentarius*-Ag nanoparticles comprising a FCC structure and/or an average diameter or broadest dimension ranging from 5, 10, 20, 30, 40, 50, 60, 70, 80, 90, 100, 110 to 120, and/or which comprise at least one of three different types of Ag species: $Ag^+$, $Ag_n^{\delta+}$ and $Ag^0$.

*Fomes fomentarius*-Ag nanoparticles or —$TiO_2$ nanoparticles may be incorporated into a composition that includes a pharmaceutically acceptable carrier or excipient, and/or additional active ingredients such as antibiotics or anticancer drugs.

In some embodiments, the composition will further comprise a soap, surfactant, bleach, hydrogen peroxide, or other cleaner.

In other embodiments, the composition may comprise medical equipment or supplies, such as cloth or paper to which the composition has been applied.

Another aspect of this technology is directed to a method for making *Fomes fomentarius*-Ag nanoparticles or *Fomes fomentarius*-$TiO_2$ nanoparticles comprising, consisting essentially of, or consisting of combining an aqueous extract of *Fomes fomentarius* with silver nitrate under conditions suitable for producing *Fomes fomentarius*-Ag nanoparticles; or combining an aqueous extract of *Fomes fomentarius* with titanium isopropoxide under conditions suitable for producing *Fomes fomentarius*-$TiO_2$ nanoparticles. Preferably, this method is performed using a clarified or isolated aqueous extract of *Fomes fomentarius* extract and without the use of reducing agents and at a temperature no more than 0, 10, 20, 25, 30 or 35° C.

In some embodiments, dried *F. fomentarious* sample (or *Fomitopsis pinicola* sample) is mixed at a ratio of 5-10 gr sample to 50 to 100 ml water. This mixture is sonicated for a sufficient time to disrupt the sample, preferably about 20-30 minutes and then centrifuged for a time and at a force sufficient to separate solid and liquid components, for example, at 2000-4000 rpm in a standard laboratory or table top centrifuge. The sonication may be performed on ice to prevent heating. Alternatively, the disrupted sample may be filtered through a filter with a pore size sufficient to separate the solid and liquid fractions of the disrupted sample. The sonication, centrifugation or filtration and subsequent storage of the extract may be performed at a temperature ranging from 0, 4, 5, 10, 15, 20, to −25° C. Preferably, the extract is stored at about 4° C. In some embodiments, Ag nanoparticles are produced by mixing at a ratio of 1-10 ml of the filtrate to 50-100 ml of 1 mM silver nitrate solution and agitated or shaken at a temperature suitable for formation of nanoparticles, for example, at room temperature. In other embodiments, a similar process may be used to produce $TiO_2$ nanoparticles using titanium isopropoxide or other metallic nitrates such as cerium nitrate, gold nitrate or iron nitrate to produce the corresponding nanoparticles.

In some embodiments, nanoparticle size may be selected by adjusting the conditions of mushroom cultivations, concentration of reactants, such as silver nitrate or titanium isopropoxide, or mushroom extract (e.g., by desiccation, dialysis, etc.), the incubation time of a mixture of these substrates and the mushroom extracts, selection of a medium or pH.

Another aspect of the present disclosure is a method for treating a microbial infection or cancer comprising, consisting essentially of, or consisting of administering to a subject in need thereof at least one of *Fomitopsis pinicola*-$TiO_2$-nanoparticles or *Fomitopsis pinicola*-Ag nanoparticles in an amount sufficient to inhibit growth or viability of a microorganism or proliferation or viability of the cancer.

The Ag and $TiO_2$ nanoparticles disclosed herein contain components of *Fomitopsis pinicola* ("mushroom extract") as shown by FT-IR. This is demonstrated, for example, by the presence of amino and hydroxyl groups in the nanoparticles. Preferably, the nanoparticles disclosed herein substantially conform to the FT-IR spectra described herein. However, in some embodiments, these FT-IR spectra may vary.

Preferably, the $TiO_2$ nanoparticles exhibit by Fourier transform infrared (FT-IR) spectroscopy adsorption at 1000, 1414, and 1644 $cm^{-1}$ respectively corresponding to C=N, C—N and ($TiO_2$, OH and C=O); and the Ag nanoparticles exhibit by Fourier transform infrared (FT-IR) spectroscopy peak absorption of linear aliphatic amines (C—N) at 1000-1040 $cm^{-1}$. The inventors also observed that the nanoparticles produced using the green synthesis methods disclosed herein using the two mushroom extracts, and not with chemical reducing agents, exhibited broader absorption, for example, a broader absorption corresponding to the presence of different Ag or $TiO_2$ species.

In some embodiments *Fomitopsis pinicola*-Ag nanoparticles comprising fcc crystals and/or having average diameter or broadest dimension ranging 5, 10, 20, 30, 40, 50, 60, 70, 80, 90, 100, 110 to 120 nm are administered. Preferably, the Ag nanoparticles range in diameter or broadest dimension between 10 and 30 nm. The Ag nanoparticles may also comprise at least one of three different types of Ag species: $Ag^+$, $Ag_n^{\delta+}$ and $Ag^0$. The presence of three Ag species distinguishes the AgNPs disclosed herein from other types of Ag nanoparticles and contributes to the antimicrobial or antibacterial activity of the AgNPs.

In other embodiments, *Fomitopsis pinicola*-$TiO_2$ nanoparticles comprise a rutile phase and/or have an average diameter ranging from 5, 10, 20, 30, 40, 50, 60, 70, 80, 90, 100, 110 to 120 nm are administered. Preferably, the $TiO_2$ nanoparticles range in diameter or broadest dimension between 10 and 80 nm. The $TiO_2$ nanoparticles may comprise $Ti^{4+}$ species corresponding to a tetrahedral coordination. $TiO_2$ NPs of different species such as dispersed tetrahedral $TiO_2$, octahedral, rutile and agglomerated form were observed.

In some embodiments, the *Fomitopsis pinicola*-$TiO_2$ nanoparticles are made using an aqueous extract of *Fomitopsis pinicola* and titanium isopropoxide. This extract is preferably clarified or filtered to remove solid components. For example, it may be clarified by centrifugation to pellet and remove solid components or may be filtered through a 0.2 or 0.45 µm filter. Preferably, the extract is produced at less than 15, 20, 25, 30, or 35° C. and exhibits reducing activity sufficient to produce nanoparticles. In preferred embodiments, no other reducing agents such as sodium citrate, sodium borohydride, lithium aluminum hydride, sulfur dioxide, thiosulfates, iodides, hydrogen peroxide, hydrazine, diisobutylaluminum hydride, DTT, cyanides are required thus reducing the impact of harmful chemicals on the environment and provided added safety during preparation.

In other embodiments, *Fomitopsis pinicola*-Ag nanoparticles are made using an aqueous extract of *Fomitopsis pinicola* and silver nitrate. This extract is preferably clarified or filtered to remove solid components. For example, it may be clarified by centrifugation to pellet and remove solid components or may be filtered through a 0.2 or 0.45 µm filter. Preferably, the extract is produced at less than or equal to 0, 5, 10, 15, 20, 25, 30, or 35° C. and exhibits reducing activity.

This method may be used to prevent or treat a subject having a bacterial infection, including but not limited to Gram-negative and Gram-positive infections or to reduce the risk of exposure of a subject to bacteria, for example, by sanitizing skin or medical supplies or instruments. Bacterial infections include but are not limited to those caused by *staphylococcus* such as *Staphylococcus aureus*, by *streptococcus*, such as *Streptococcus pyogenes*, by *Pseudomonas* or by *Corynebacterium*. Skin infections caused by these or other bacteria include cellulitis, erysipelas, bacterial folliculitis, hot tub folliculitis, furuncles, carbuncles, impetigo, erythrasma, and Methicillin-resistant *Staphylococcus aureus* (MRSA) skin infections. Other bacterial infections such as those associated with abrasions, lacerations, punctures, and other wounds, and eye, sinus, respiratory, enteric infections such as food poisoning, STDs (including *chlamydia*, syphilis, gonorrhea) and other internal infections may be treated by bringing bacteria into contact with the *Fomitopsis pinicola* Ag or $TiO_2$ nanoparticles described herein. The above mentioned conditions may also be prophylactically treated or sanitized using compositions containing the Ag or $TiO_2$ nanoparticles disclosed herein.

The *Fomitopsis pinicola* Ag and $TiO_2$ nanoparticle based methods disclosed herein may be used to prevent or treat a subject having a neoplasm, tumor, or cancer, including but not limited to colon or colorectal cancer, breast cancer, lung cancer, prostate cancer, melanoma, bladder cancer, kidney cancer, endometrial cancer, leukemia, pancreatic cancer, thyroid cancer, liver or interhepatic bile duct cancer, or brain cancer.

Another aspect of this technology is directed to *Fomitopsis pinicola*-$TiO_2$ nanoparticles comprising a rutile phase and/or which have an average diameter or broadest dimension ranging from 5, 10, 20, 30, 40, 50, 60, 70, 80, 90, 100, 110 to 120 nm, and/or which exhibit $Ti^{4+}$ coordination.

Another aspect of this technology is directed to or *Fomitopsis pinicola*-Ag nanoparticles comprising a FCC structure and/or an average diameter or broadest dimension ranging from 5, 10, 20, 30, 40, 50, 60, 70, 80, 90, 100, 110 to 120, and/or which comprise at least one of three different types of Ag species: $Ag^+$, $Ag_n^{\delta+}$ and $Ag^0$.

*Fomitopsis pinicola*-Ag nanoparticles or $TiO_2$ nanoparticles may be incorporated into a composition that includes a pharmaceutically acceptable carrier or excipient, and/or additional active ingredients such as antibiotics or anticancer drugs.

In some embodiments, the composition will further comprise a surfactant, bleach, hydrogen peroxide, or other cleaner.

In other embodiments, the composition may comprise medical equipment or supplies, such as cloth or paper to which the composition has been applied.

Another aspect of the present disclosure is directed to a method for making *Fomitopsis pinicola*-Ag nanoparticles or *Fomitopsis pinicola*-$TiO_2$ nanoparticles comprising, consisting essentially of, or consisting of combining an aqueous extract of *Fomitopsis pinicola* with silver nitrate under conditions suitable for producing *Fomitopsis pinicola*-Ag nanoparticles; or combining an aqueous extract of *Fomitopsis pinicola* with titanium isopropoxide under conditions suitable for producing *Fomitopsis pinicola*-$TiO_2$ nanoparticles. Preferably, this method is performed using a clarified or isolated aqueous extract of *Fomitopsis pinicola* extract and without the use of reducing agents and at a temperature no more than 0, 10, 20, 25, 30 or 35° C.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1A. Photographs of brown rot basidiomycetes—*F. fomentarius*—under view showing pores.

FIG. 1B shows basidiospores at 100×.

FIG. 2. Powder X-ray diffraction spectra of *Fomes fomentarius* (a) Ag nanoparticles (NPs) and (b) $TiO_2NPs$. The spectra (a) represents AgNPs with face centered cubic (fcc) structure and (b) shows $TiO_2NPs$ crystals with rutile phase.

FIG. 6A shows zone of inhibition (ZOI) by agar well diffusion for *Fomes fomentarius* $TiO_2NPs$ and AgNPs for *E. coli*.

FIG. 6B shows zone of inhibition (ZOI) by agar well diffusion for *Fomes fomentarius* $TiO_2NPs$ and AgNPs for *S. aureus*.

FIG. 6C. Bar graph comparing ZOIs for *Fomes fomentarius* $TiO_2NPs$ and AgNPs.

FIG. 8A. SEM micrograph of *S. aureus*: control (untreated) cells.

FIG. 8B. SEM micrograph of *S. aureus*: cells treated with *Fomes fomentarius* AgNPs at 100 μg/mL.

FIG. 8C. SEM micrograph of *S. aureus*: cells treated with *Fomes fomentarius* $TiO_2NPs$ at 100 μg/mL.

FIG. 9E. Cell viability by MTT Assay. The HCT-116 cells treated with different concentrations of *Fomes fomentarius* AgNPs after 48 h. Difference between two treatment groups were analyzed by student's t test where ** $p<0.01$.

FIG. 20A shows the cellular morphology of HCT-116 control cells by light microscopy.

FIG. 20B shows the cellular morphology of HCT-116 cells treated with 8.0 μg $mL^{-1}$ *F. pinicola* $TiO_2NPs$ by light microscopy.

FIG. 20C shows the cellular morphology of HCT-116 control cells by light microscopy. confocal scanning microscopy.

FIG. 20D shows the cellular morphology of HCT-116 cells treated with 8.0 μg $mL^{-1}$ *F. pinicola* $TiO_2NPs$ by confocal scanning microscopy.

DETAILED DESCRIPTION OF THE INVENTION

Figure 3:
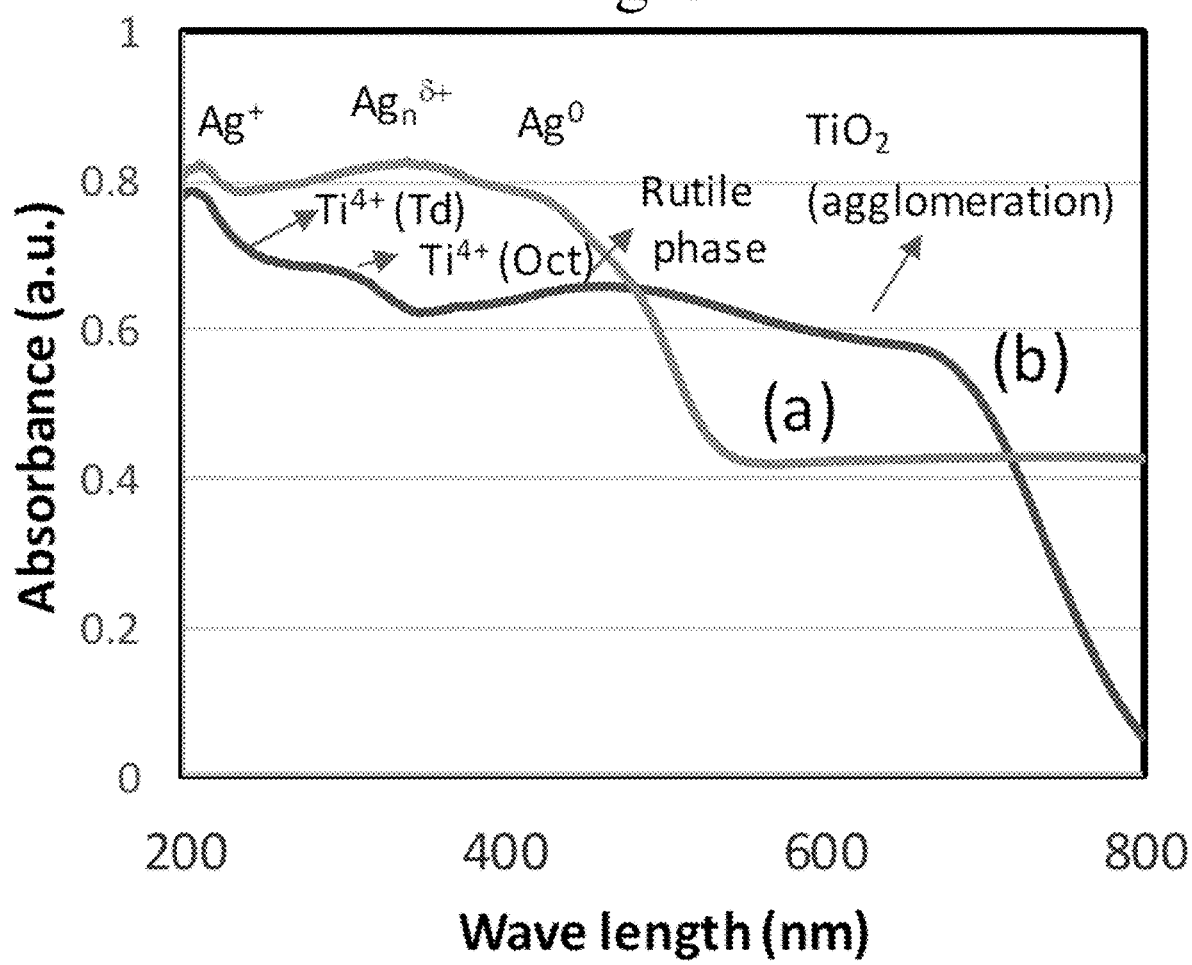
FIG. 3. Diffuse reflectance UV-visible spectra of *Fomes fomentarius* (a) AgNPs and (b) $TiO_2NPs$. The spectra (a) shows existence of $Ag^+$, $Ag_n^{\delta+}$ and $Ag^0$ species and (b) shows isolated Ti(IV), Octahedral Ti and rutile phase of $TiO_2NPs$.

The present disclosure describes a green, bio-directed process for synthesis of silver nanoparticles (AgNPs) and titanium oxide (TiO$_2$) nanoparticles from an amalgamation of aqueous extracts of *Fomes fomentarius* or *Fomitopsis pinicola* and silver nitrate or titanium (iv) isopropoxide.

*F. fomentarius* was identified phenotypically and by 18S ribosomal RNA gene sequencing (Gene accession no: MK635351) and *F. pinicola* by 18S ribosomal RNA gene sequencing (Gene accession no MK635350).

Aqueous extracts or aqueous-alcohol (e.g., aqueous methanol or ethanol) extracts may be produced by homogenizing, macerating, sonicating or otherwise disrupting samples of these fungi and suspending the material in water or an aqueous buffer, including but not limited to aqueous methanol or aqueous ethanol. Alcohol content can vary between 0, 10, 20, 30, 40, 50, 60, 70 80, 90 o>90% by volume. In a preferred embodiment, fungal material is dried and powdered prior to extraction. The extract is preferably clarified by removal of solid components, for example, by filtration or centrifugation prior to use. However, in some embodiments, nanoparticles of solid fungal material may be retained in an extract, for example, particles ranging in size <1, 1, 2, 5, 10, 20, 50, 100, 200, 500 or <1,000 nm in diameter or broadest dimension. Preferably the extract is produced and stored at a temperature less than 30, 25, 20, 15, 10, 5 or 0° C.

Silver and titanium oxide nanoparticles may be produced by amalgamating or contacting an aqueous fungal extract with silver nitrate (or other silver salts) or titanium isopropoxide (or other titanium salts, such as titanium sulfate salts, nitrate salts, chloride salts and oxide salts) for a time and under conditions sufficient to form silver nanoparticles or titanium oxide nanoparticles from the amalgamated mixture of fungal extract of silver nitrate or titanium isopropoxide. The nanoparticles once formed may be separated from the liquid components of the amalgamation and washed and resuspended.

The biosynthesis of the TiO$_2$ and AgNPs were studied and characterized by X-ray diffraction (XRD), diffuse reflectance UV-Visible spectroscopy (DR-UV), Fourier transform infrared spectroscopy (FT-IR), scanning electron microscopy (SEM) and transmission electron microscope (TEM).

The inventors found that nanoparticle size could be controlled by altering the concentration of AgNO$_3$ or titanium isopropoxide, altering the concentration of the mushroom extracts, altering the length of incubation time of the nanoparticle precursor, and/or decreasing or increasing the pH during incubation. Success was achieved in obtaining NPs of differing sizes and shapes, for example it is possible to produce a TiO$_2$ nanoparticle having approximately the same 10-20 or 10-30 nm average diameter as the Ag NPs.

The antibacterial and anticancer activities of the TiO$_2$ and AgNPs made with *F. fomentarius* extracts were significant with morphological damage being caused by both, although AgNPs (10-20 nm) were found to have greater effects on bacterial and cancer cells in comparison to TiO$_2$NPs (100-120 nm in average diameter).

The antibacterial and anticancer activities of the TiO$_2$ and AgNPs made with *F. pinicola*, were significant, however, enhanced antibacterial and anticancer actions were seen with AgNPs (10-30 nm in average diameter).

TiO$_2$ and AgNPs synthesized using *F. fomentarius* and *F. pinicola* extracts, have numerous biomedical applications in biomedicine due to an effective enzyme combination which permits them to modify different chemical compounds more safely or into less toxic forms as required for ecofriendly and safe biomaterials.

Modes of administration. The methods of administering the nanoparticles or compositions containing them disclosed herein may comprise administering a silver or titanium oxide nanoparticle composition or composition intravenously, intramuscularly, topically (e.g. on or into a wound or precancerous or cancerous lesion), intradermally, into or over a wound, intramucosally, subcutaneously, sublingually, orally, intravaginally, intracavernously, intraocularly, intranasally, intrarectally, gastrointestinally, intraductally, intrathecally, subdurally, extradurally, intraventricular, intrapulmonary, into an abscess, intra articularly, into a bursa, subpericardially, into an axilla, intrauterine, into the pleural space, intraperitoneally, transmucosally, or transdermally.

Carriers/Excipients. The term carrier encompasses any excipient, binder, diluent, filler, salt, buffer, solubilizer, lipid, stabilizer, or other material well known in the art for use in pharmaceutical formulations, for example, for intravenous administration a carrier may be sodium chloride 0.9% or mixtures of normal saline with glucose or mannose. The choice of a carrier for use in a composition will depend upon the intended route of administration for the composition. The preparation of pharmaceutically acceptable carriers and formulations containing these materials is described in, e.g., *Remington's Pharmaceutical Sciences,* 21st Edition, ed. University of the Sciences in Philadelphia, Lippincott, Williams & Wilkins, Philadelphia Pa., 2005, which is incorporated herein by reference in its entirety.

Formulations for administration. For therapeutic purposes, formulations for parenteral administration can be in the form of aqueous or non-aqueous isotonic sterile injection solutions or suspensions. The term parenteral, as used herein, includes intravenous, intravesical, intraperitoneal, subcutaneous, intramuscular, intralesional, intracranial, intrapulmonal, intracardial, intrasternal, and sublingual injections, or infusion techniques.

Topical administration. Formulations for topical administration to the skin, wounds, burns, or mucous membranes include, for example, ointments, creams, gels and pastes comprising the composition in a pharmaceutical acceptable carrier. The formulation of the composition for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Oral administration. Solid preparations for oral administration may include a tablet, a pill, a powder, a granule, a capsule, and the like. These solid preparations may be prepared by mixing at least one excipient, such as starch, calcium carbonate, sucrose, lactose, or gelatin, with nanoparticle as disclosed herein. In addition to such a simple excipient, lubricants, such as magnesium stearate and talc, may be used. Liquid preparations containing nanoparticles for oral administration correspond to a suspension, a liquid for internal use, oil, syrup, and the like, and may include several types of excipient, for example, a wetting agent, a sweetener, an aroma, a preservative, and the like, in addition to simple diluents that are frequently used, such as water and liquid paraffin.

Parenteral administration. Injectable preparations, for example, sterile injectable aqueous or oleaginous suspensions containing nanoparticles can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and nonionic detergents, polyethylene glycols can be used. Mixtures of solvents and wetting ingredients such as those discussed above are also useful.

Respiratory system administration. Administration to the respiratory system may be accomplished using a drug delivery device such as a nebulizer to administer a nanoparticle composition as disclosed herein, in an inhalable form. Nebulizers include soft mist inhalers, jet nebulizers, ultrasonic wave nebulizers, and nebulizers using vibrating mesh technology. A metered-dosage inhaler is another drug delivery device that delivers a selected or metered amount of a medication, such as the nanoparticle compositions disclosed herein. Typically, this device produces and releases an aerosol of micrometer-sized particles that are inhaled.

Thus, preferably, the nanoparticles are sized so as to provide a uniform dosage or so they are absorbed in a particular part of the respiratory system. In some cases, the particles may be a dry powder in others as a mist or in a semiliquid form. Metered-dose inhalers and their various components, propellants, excipients and other elements are described by and incorporated by reference to hypertext transfer protocol secure://en.wikipedia.org/wiki/Metered-dose_inhaler. An inhalable composition may be formulated in the form of a hydrofluoroalkane inhaler or HFA (metered dose inhaler or MDI), dry powder inhaler (DPI), or as a nebulizer solution.

Dose. The dose of a nanoparticle composition as disclosed herein with respect to the human or animal body may vary depending on patient's age, body weight, and gender, the form of administration, state of health, and severity of disease. The dose may be generally 0.01-100 mg/kg/day, preferably 0.1-20 mg/kg/day, and more preferably 5-10 mg/kg/day. The composition may also be divisionally administered at predetermined intervals according to the determination of a doctor or pharmacist.

Antibiotics which may be further incorporated into a nanoparticle composition or coadminstered therewith, include but are not limited to the following. Penicillins for example, phenoxymethylpenicillin, flucloxacillin and amoxicillin; Cephalosporins for example, cefaclor, cefadroxil and cefalexin; Tetracyclines for example, tetracycline, doxycycline and lymecycline. Aminoglycosides—for example, gentamicin and tobramycin; and Macrolides—for example, erythromycin, azithromycin and clarithromycin. One or more antibiotic may be administered in combination with an Ag or $TiO_2$ nanoparticle as disclosed herein.

Anti-cancer drugs. The Ag and $TiO_2$ fungal nanoparticles disclosed herein may be administered with cancer chemotherapeutics including but not limited to alkylating agents, antimetabolites, topoisomerase inhibitors, antibiotics, mitotic inhibitors, and protein kinase inhibitors. Specific anti-cancer drugs include but are not limited to Avastin (Bevacizumab), Bevacizumab, Camptosar (Irinotecan Hydrochloride), Capecitabine, Cetuximab, Cyramza (Ramucirumab), Eloxatin (Oxaliplatin), Erbitux (Cetuximab), 5-FU (Fluorouracil Injection), Fluorouracil Injection, Ipilimumab, Irinotecan Hydrochloride, Keytruda (Pembrolizumab), Leucovorin Calcium, Lonsurf (Trifluridine and Tipiracil Hydrochloride), Mvasi (Bevacizumab), Nivolumab, Opdivo (Nivolumab), Oxaliplatin, Panitumumab, Pembrolizumab, Ramucirumab, Regorafenib, Stivarga (Regorafenib), Trifluridine and Tipiracil Hydrochloride, Vectibix (Panitumumab), Xeloda (Capecitabine), Yervoy (Ipilimumab), Zaltrap (Ziv-Aflibercept), Zirabev (Bevacizumab), and Ziv-Aflibercept.

Cosmetics. Medical or cosmetic amorphous formulations in the form of creams, lotions, ointments, gels, shampoos, conditioners, moisturizers, or antiperspirants can be readily prepared by blending in the antimicrobial AgNPs or $TiO_2$ NPs as disclosed herein. Preparations such as the serums, creams, lotions, gels, shampoos, conditioners, emulsions, salves or ointments, and antiperspirants are known to those ordinarily skilled in the art.

Other compositions. The nanoparticle compositions as disclosed herein can be used in other compositions where an antimicrobial environment is desired or where a reduction in microbial growth, or a reduction in odor would be useful. For example, the silver or $TiO_2$ nanoparticles compositions may be added to cleaners, laundry or dishwashing detergents, paints, cosmetics, on wound dressings to control of odor from wound exudates, in dental compositions, in products used in bowel or vascular surgery, oral hygiene products, bathroom products, textile products, coatings, natural or synthetic polymers adhesives, paint products, polymer films, paper, leather, rubber and plastic articles. Unfinished and finished articles such as yarn or bolts of cloth may also be rendered antimicrobial.

Example 1

Nanoparticles Made with *Fomes fomentarius*

Collection, Phenotypic and Genotypic Studies of *Fomes fomentarius*. For the collection of sporocarps, a standard method was followed, see Krueger, D. *Monographic Studies in the Genus Polyporus (Basidiomycotina)*. Incorporated by reference and available online: hypertext transfer protocol-secure://trace.tennessee.edu/utk_graddiss/2135/ (accessed on 6 Apr. 2021). Photographs were taken by a Nikon D5300 DSLR Camera (Nikon, Tokyo, Japan) with a zoom lens of 18-140 VR (data of sampling in supplementary file). Passport data and the microhabitat characteristics of collected samples has Biomolecules 2020, 10, 622 3 of 15 been recorded in the field book. Samples were properly labeled, given a voucher number and carried to the laboratory for detailed morphometric examination. Collected specimens were identified by keen observation of structures like pileus, stipe, their shape, structure, gill attachment, etc., using standard keys (e.g., Mycokey, Index fungoram etc.) field guides and manuals.

The samples were dried and deposited at the herbarium of the Centre for Biodiversity and Taxonomy, University of Kashmir, J&K, India. Microscopic features and measurements were made from slides that were prepared and stained with lactophenol cotton Blue, 2% KOH and Melzer's reagent. For examination, the spores were tapped off the razor blade onto a clean slide and a drop of KOH or Melzer's reagent was added. Observation and photographs were captured at magnification between ×40 to ×100 using a Nikon Eclipse 80i microscope and phase contrast illumination (Nikon, Tokyo, Japan).

Isolation and PCR DNA extraction was done using the manual CTAB method (cetyl trimethylammonium bromide); Mohanta, Y.; et al., *Silver nanoparticles synthesized using wild mushroom show potential antimicrobial activities against food borne pathogens*. MOLECULES 2018, 23, 655, incorporated by reference.

The extracted DNA was dissolved and preserved in TE (Tris-EDTA) buffer. The amplification was carried out for internal transcribed spacer (ITS) regions using the ITS1 and ITS4 in a PCR System Thermocycler Applied Biosystems with following parameters—10 min of initial denaturation at 95° C., 35 cycles at 95° C. for 1 min, 54° C. for 30 s and 72° C. for 2 min, followed by extension at 72° C. for 10 min. The purification of amplified products was done and sequenced with the same primers.

The DNA sequences were submitted to GeneBank and analyzed for homology using BLAST on NCBI (Table 1); Felsenstein, J. PHYLIP (Phylogeny Inference Package), Version 3.57 c. Available online: hypertext transfer protocol://www.dbbm.fiocruz.br/molbiol/main.html (accessed on 6 Apr. 2021).

Sequence and Phylogeny Analysis. Wild mushroom was identified by ribosomal gene analysis. The small subunit sequences were aligned with additional sequences downloaded from NCBI GenBank (hypertext transfer protocol:// ncbi.nim.nih.gov) using BioEdit Sequence Alignment Editor (version 7.2.5). The sequence alignments and phylogenetic analysis were performed using MEGA 10 software (Tamura et al., 2011). Phylogeny was studied on ITS-18S rRNA genes by maximum likelihood method. Initial alignment was done using Clustal W software for maximum alignment and minimum gaps. The tree was generated by using the program DNADIST and NEIGHBOR from PHYLIP 3.69, Felsenstein, J. et al., supra.

Biosynthesis of $TiO_2$ and AgNPs Using Fomes Fomentarius. The synthesis of $TiO_2$ and AgNPs was conducted using the extract of *F. fomentarius* by adopting a green synthesis method; see Mohanta, Y.; et al., *Silver nanoparticles synthesized using wild mushroom show potential antimicrobial activities against food borne pathogens*. MOLECULES 2018, 23, 655, incorporated by reference.

The *F. fomentarius* sample was dried to obtain powder (10 g), which was further mixed with 100 mL of millipore water and sonicated for 25-30 min. The mixture was further centrifuged at 4000 rpm to obtain the clarified solution. Subsequently, solution was filtered and stored at 4° C. A total of 10 mL of filtrate was mixed with 1 mM $AgNO_3$ (100 mL) and put at room temperature on a shaker for agitation under observation, until the appearance of color change (10 min). A similar procedure was followed for $TiO_2$NPs, where 100 mL of 1 mM Titanium (IV) isopropoxide was used as a source solution. The mechanism involved in the production of antimicrobial and anti-cancer NPs using *F. fomentarious* mushroom extract is unclear.

Characterization of Biosynthesized $TiO_2$ and AgNPs. The crystalline phase of the $TiO_2$ and AgNPs was measured using a benchtop X-ray powder diffractometer MiniFlex 600 (Rigaku, Shibuya, Tokyo, Japan). The sample was measured in 2 theta range 5-80°, with step size of 0.02° and scan rate of 1°/min.

The coordination environment of $TiO_2$ and AgNPs were analyzed using diffuse reflectance UV-Visible spectroscopy (V-750, JASCO). The sample for diffuse reflectance was prepared by dispersing the sample in a spherical disc with an integrated sphere (60 mm dia, ISV-922). After pressing, the sample with 0.5 mm thickness was scanned between wavelength range 200-870 nm.

The $TiO_2$ and AgNPs functional groups were analyzed using Fourier transform infrared spectroscopy equipped with attenuated total reflectance (ATR) (Perkin Elmer, Arcata, CA, USA).

The surface morphology, distribution and features of $TiO_2$ and AgNPs were studied using scanning electron microscopy (SEM) (Inspect S50) and transmission electron microscope (TEM) (Morgagni 268).

For TEM analysis, samples were prepared by dispersing in ethanol followed by shaking in an ultrasonicator for 20 min, and then a suspended drop was dried at room temperature on the carbon-coated copper grid; see Rehman, S.; et al., *Isolation and characterization of a novel thermophile; Bacillus haynesii, applied for the green synthesis of ZnO nanoparticles*. ARTIF. CELLS NANOMED. BIOTECHNOL. 2019, 47, 2072-2082, incorporated by reference.

Antibacterial Activity of Biosynthesized NPs. Common pathogenic bacteria *Escherichia coli* (*E. coli* ATCC35218) and *Staphylococcus aureus* (*S. aureus* ATCC29213) were used for the antibacterial activity of synthesized $TiO_2$ and AgNPs by agar well diffusion. The bacterial strains were maintained on nutrient agar media (NA).

In preparation for the antibacterial study, a homogeneous water suspension of the NPs was prepared by sonication for 15-20 min at 30° C. Test organisms grown at 37° C. for 18 h in Mueller Hinton (MHB) were adjusted to the cell density of 106 CFU/mL. A total of 100 µL of adjusted inoculum of each bacterial strain was inoculated on the MHA plates. After 20-30 min, the dried plates were punched for wells using the sterile borer. A total of 50 µL of $TiO_2$NP and AgNP (100 µg/mL) suspension was placed into the wells. Sterile water was used as a negative control. This was followed by the incubation at 37° C. for 24 h. The activity of the synthesized NPs was evaluated by measuring the zone of inhibition zone around the wells in millimeters (mm); see Rehman, S.; et al., supra, incorporated by reference.

Topological Changes in Treated Bacteria by SEM. Additionally, the treated *E. coli* and *S. aureus* were studied by SEM for the morphological and physiological alteration caused by NPs. Precisely, adjusted bacterial cells were treated with 100 µg/mL of $TiO_2$ and AgNPs and further incubated at 37° C. for overnight. Later, the incubated mixture was centrifuged at 12,000 rpm for 10 min for treated and untreated cells. The harvested cells were thrice washed using PBS and primarily fixed with 2.5% glutaraldehyde for 4 h followed by fixation with 1% osmium tetroxide for 2 h. Cells were washed multiple times and further dehydrated by varying concentrations of ethanol (50%, 70%, 90%, 100%). The cells were placed onto the aluminum stubs and dried using a desecrator. Finally, gold coating was done and cells were examined by SEM at an accelerating voltage of 20 kV; Rehman, S.; et al., *Antibacterial and Antifungal Activity of Novel Synthesized Neodymium-Substituted Cobalt Ferrite Nanoparticles for Biomedical Application*. PROCESSES 2019, 7, 714, incorporated by reference.

Cytotoxic Activity: Cell Culture & Treatments. Human colorectal carcinoma cells (HCT-116) were used for the study. DMEM medium was used, which was supplemented with 10% fetal bovine serum (FBS); (10%) L-glutamine; 10% selenium chloride; 120 μg/mL and streptomycin; and 120 Unit/mL penicillin in a 5% CO2 incubator (Thermo Scientific Heracell-150, Langenselbold Germany) at a temperature of 37° C. The cells with more than 70-80% confluency were used for the $TiO_2$ and AgNPs treatments. The treatment of HCT-116 cells was carried out with different concentrations of NPs ranging from 0.5 to 8.0 μg/mL. The cells were analyzed after a time span of 48 h. The experiment was carried out in triplicate for statistical analysis; see Khan, F.; et al., *FMSP-nanoparticles induced cell death on human breast adenocarcinoma cell line (MCF-7 Cells): Morphometric analysis*. BIOMOLECULES 2018, 8, 32, incorporated by reference.

Cancer Cell Morphology. The cell morphology of untreated and treated HCT-116 cells was examined post-48 h under an inverted microscope (TS100E-Eclipse, Nikon, Tokya, Japan) and compared under 200× magnification.

Cytotoxicity by MTT Assay. The cells with confluency of 70-80% in 96-well cell culture plates were subjected to MTT assay. After 48 h, MTT (5 mg/mL) was added in all the wells and kept for 4 h. Later, DMSO was added and the plate was read in an ELISA Plate Reader 570 nm wavelength (Biotek Instruments, Winooski, VT, USA).

The (%) percentage of cell viability was calculated as per given formula: Cell Viabilty %=(A/B)×100 where A is optical density of nanoparticles, and B be is optical density of controls.

Nuclear Staining by DAPI. The cells were stained with DAPI staining to study the effect of $TiO_2$NPs and AgNPs on the cell nucleus. After 48 h, the treated and untreated HCT-116 cells were immersed in ice-cold (4%) paraformaldehyde. Later, the cells were added with Triton X-100 and prepared in PBS for 5 min to premetallize the cell membrane. The cells were stained using DAPI (5 μg/mL) in PBS, prepared in dark. Washing with Triton X-100 was done, followed by examining the nuclear morphology under confocal scanning microscope (Zeiss, Jena, Germany) equipped with a digital camera; See Anthony, K. J. P.; et al. *Synthesis of silver nanoparticles using pine mushroom extract. A potential antimicrobial agent against E. coli and B. subtilis*. J. IND. ENG. CHEM. 2014, 20, 2325-2331, incorporated by reference.

Phenotypic and Genotypic Work with *F. fomentarius*. Whether extracts of *F. fomentarius* collected from an angiosperm host in the natural forest of Kashmir valley, India extracts could be employed for the synthesis of $TiO_2$ and AgNPs was evaluated. The basidiomes of *F. fomentarius* are perennial, leathery and hoof-shaped. The above surface is smooth and zoned, having a thick crust, and the lower surface is pale brown and concave in shape (FIG. 1A). The microscopic observations were mainly focused on basidiospores, which were cylindrical to ellipsoid in shape, measuring 36×1.5 to 2 μm. Spores are bilaterally asymmetrical (inequilateral), as they are forcibly discharged from the basidium for dispersal. The shape of the hilar appendix is beaked. The spore apex is rounded. Spore ornamentation is smooth (FIG. 1B).

The ITS1-ITS4 sequences of *F. fomentarius* were deposited in the NCBI Gene Bank under accession number MK635351. The phylogenetic relationships with related strains are shown in Table 1. The term *Fomes fomentarius* as used herein describes the strain deposited under MK635351 as well as related strains, such as those described in Table 1 or those having a maximum identity of at least 99.5, 99.6, 99.7%, preferably at least 99.8, 99.9 or 100%, and/or a maximum coverage of at least 98, 99 or 100%.

TABLE 1

Gene Bank accession numbers and top BLAST match sequences of the mushroom isolates along with maximum identify and query coverage.

| | BLAST Match Sequence | | |
|---|---|---|---|
| Accession Number | Reference Accession Number | Coverage | Maximum Identity |
| MK635351 | JX126894.1 *Fomes fomentarius* | 100% | 100% |
| | KU1391991.1 *Fomes fomentarius* | 100% | 100% |
| | MK9101131 *Fomes fomentarius* | 100% | 99.82% |
| | KU863082.1 *Fomes fomentarius* | 100% | 99.82% |
| | KX065943.1 *Fomes fomentarius* | 100% | 99.82% |

Characterization of $TiO_2$ and AgNPs. FIG. 2 lines a,b show the X-ray diffraction (XRD) spectra of Ag and $TiO_2$ NPs.

In the case of AgNPs, clear diffraction lines corresponding to (111), (200) and (220) planes were observed, indicating the presence of face-centered cubic (fcc) crystals. The presence of an additional peak at a 2-theta value of about 51.2 and 52.3 and additional less indexed peaks can be ascribed due to $AgNO_3$ compounds present in the extract.

In the case of $TiO_2$NPs, the formation of crystalline $TiO_2$ was observed with sharp peaks corresponding to the rutile phase. Diffuse reflectance UV-visible spectra were recorded to study the coordination site of titanium oxide and AgNPs in the extract. FIG. 3 lines a and b show the diffuse reflectance spectra of AgNPs and $TiO_2$ NPs. The synthesized silver nanoparticle showed the presence of different oxidation states of Ag species (FIG. 3, line a). The presence of three clear bands was observed at 220, 350 and 410 nm. The small band at 220 nm was ascribed due to Ag+, while a broad band at 350 and 410 nm showed the dominant species of $Ag_n^+$ nanoclusters and $Ag^0$ species.

In the case of $TiO_2$, the band at 220 nm showed the presence of isolated Ti (IV) species, while the octahedral Ti species was found at about 300 nm. In line with XRD analysis, the sample $TiO_2$ showed the presence of a rutile (titania) phase at about 410 nm and expanded to show the presence of agglomeration among $TiO_2$ nanoparticles with broad absorption extending up to 700 nm.

Figure 4:
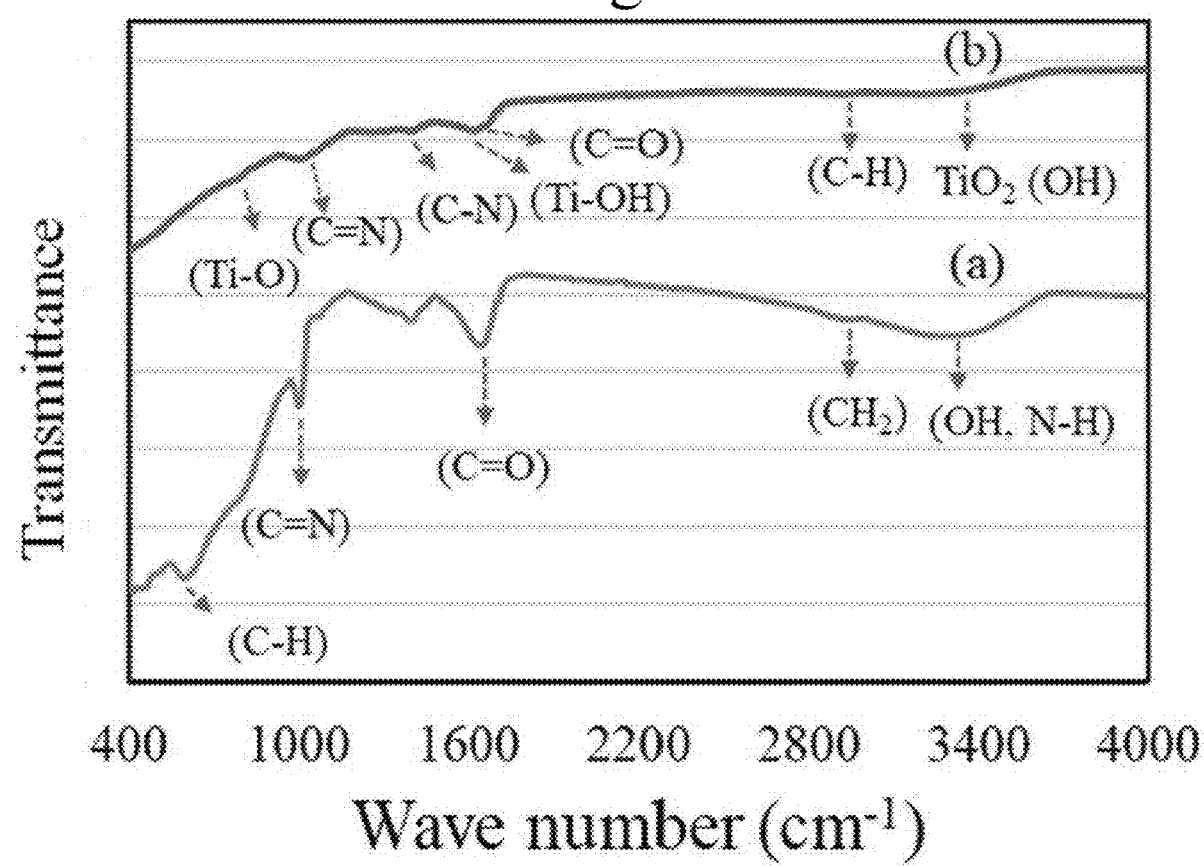
FIG. 4. Fourier transform infrared (FT-IR) spectra of *Fomes fomentarius* (a) AgNPs and (b) $TiO_2NPs$. The spectra (a,b) show the presence of various phytocomponents related to amino, methyl and hydroxyl groups assist in Ag and $TiO_2NPs$ formation.

FIG. 4, lines a and b show the Fourier transform infrared (FT-IR) spectroscopy of Ag and $TiO_2$NPs. The presence of active components like flavonoids and alkaloids in the *F. fomentarius* extract are reported to play an active role in reducing $Ag^+$ ions of a metal source to AgNPs.

A reduction in peak intensity and peak position compared to the extract indicates an effective nanoparticle formation.

In the case of the *F. fomentarius* mushroom extract, generally an intense peak appears corresponding to the presence of an amino and hydroxyl functional group.

The AgNPs exhibited a broad peak at about 3290 cm$^{-1}$ corresponding to hydroxyl (—OH) and N—H stretching of primary amines (FIG. 4, line a).

A methylene CH stretching peak was observed at 2940 cm$^{-1}$. The presence of an asymmetrical C—O stretching peak was observed at 1655 cm$^{-1}$.

The presence of aromatic and aliphatic amines (C—N) was clearly seen with an intense absorption peak at about 1406 and 1000 cm$^{-1}$.

The TiO$_2$NPs had comparatively less intense peak absorption values which were observed between 3000-3680 cm$^{-1}$ corresponding to —C—H symmetric stretching (2956 cm$^{-1}$) and the hydroxyl group of TiO$_2$ (3420 cm$^{-1}$).

The presence of a hydroxyl band Ti—OH was clearly observed at 1630 cm$^{-1}$.

Further, the presence of TiO$_2$NPs was confirmed with absorption peaks between 766-1630 cm$^{-1}$, corresponding to Ti—O, aliphatic C—N, and aromatic C=N bands.

These readings show the presence of various phytocomponents related to amino, methyl and hydroxyl groups present in the mushroom sample which participate in formation and composition of the silver and titanium oxide NPs.

As shown above and by the FT-IR spectra, the Ag and TiO$_2$ nanoparticles contain amino and hydroxyl functional groups as shown by N—H bands of primary amines and hydroxyl (—OH) band. The presence of aromatic and aliphatic amines is shown by aliphatic C—N and aromatic C=N bands.

FIG. 5 depicts SEM and TEM morphology of TiO$_2$ and AgNPs.

Figure 5A:
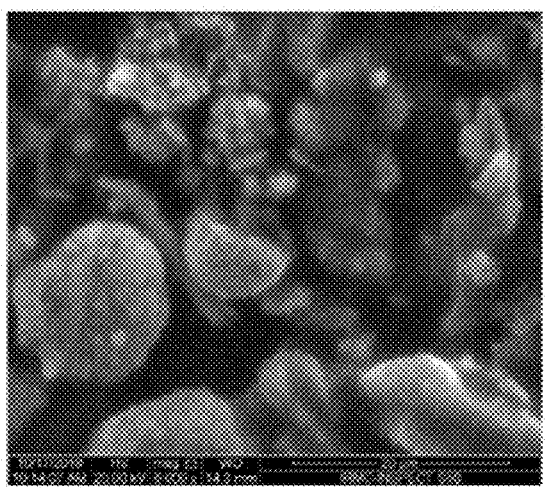
FIG. 5A shows scanning electron microscopy (SEM) of *Fomes fomentarius* $TiO_2NPs$.

FIG. 5A shows by SEM that TiO$_2$NPs were uniformly distributed on the surface with irregular shape and formation of aggregated NPs. The observed micrograph shows aggregates of TiO$_2$NPs with a rough surface.

Figure 5B:
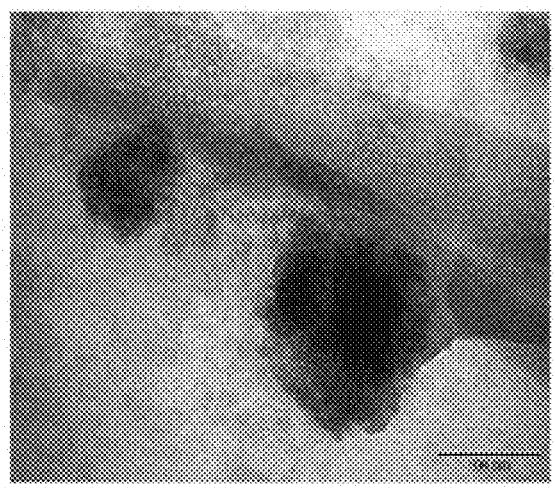
FIG. 5B shows transmission electron microscope (TEM) images of *Fomes fomentarius* $TiO_2NPs$.

As shown by FIG. 5B, the TEM micrograph of TiO$_2$ corresponded with SEM results, which showed that the prepared NPs are asymmetrical particles with an average diameter of around 80-120 nm.

Figure 5C:
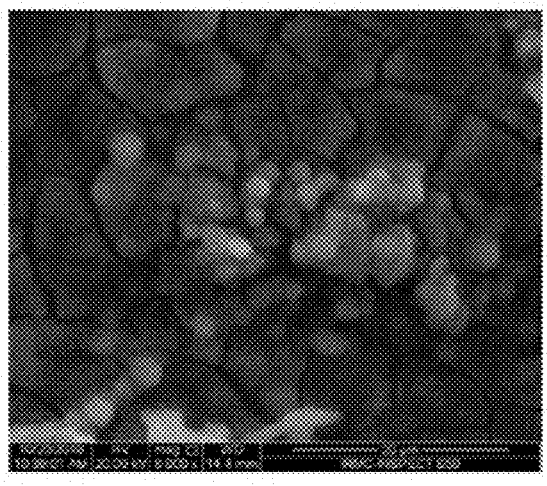
FIG. 5C shows scanning electron microscopy (SEM) of *Fomes fomentarius* AgNPs.

FIG. 5C shows by SEM that AgNPs exhibited almost a spherical shape with smooth surface conglomerated with each other.

Figure 5D:
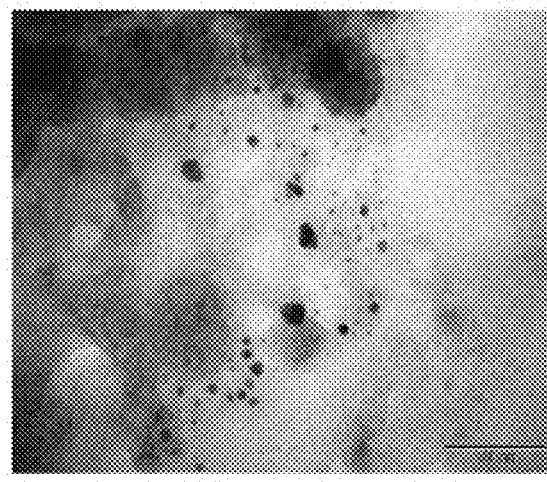
FIG. 5D shows transmission electron microscope (TEM) images of *Fomes fomentarius* AgNPs.

FIG. 5D also shows by TEM a small spherical AgNPs distributed with an average diameter of around 10-20 nm.

Antibacterial Activity of Synthesized NPs. The antibacterial activity of TiO$_2$NPs and AgNPs was evaluated by an Agar well diffusion method using *E. coli* and *S. aureus*. As shown by FIG. 6, a zone of inhibition (ZOI) around the tested AgNPs and TiO$_2$NPs was seen for both of the gram-positive and gram-negative species.

*E. coli* had a clear zone of 15 mm and 22 mm in diameter, against TiO$_2$NPs and AgNPs, respectively. Whereas *S. aureus* was observed with 11 and 15 mm of clear zones, against TiO$_2$NPs and AgNPs, respectively. The obtained results indicated that both the NPs have significant activity against both bacteria, with the elevated activity obtained against *E. coli*, when treated with AgNPs. While not being bound to a particular explanation or theory, the inventors consider that antimicrobial action may be determined by interaction of the disclosed nanoparticles with a cell, such as a bacterium and that components such as ions, from the nanoparticles are released and can diffuse into a culture medium thus exerting an antimicrobial effect.

This study of antibacterial activity of TiO$_2$NPs and AgNPs against the Gram-negative and Gram-positive bacteria showed that NPs could arrest the functioning of the cell. AgNPs were more effective obstructing agent. While not being bound to any particular theory or explanation, the inventors consider that silver ions (Ag$^+$) get released from AgNPs and interact with the phosphorus moieties in bacterial DNA, leading to inactivation of bacterial replication and growth.

Figures 7A, 7B, 7C:
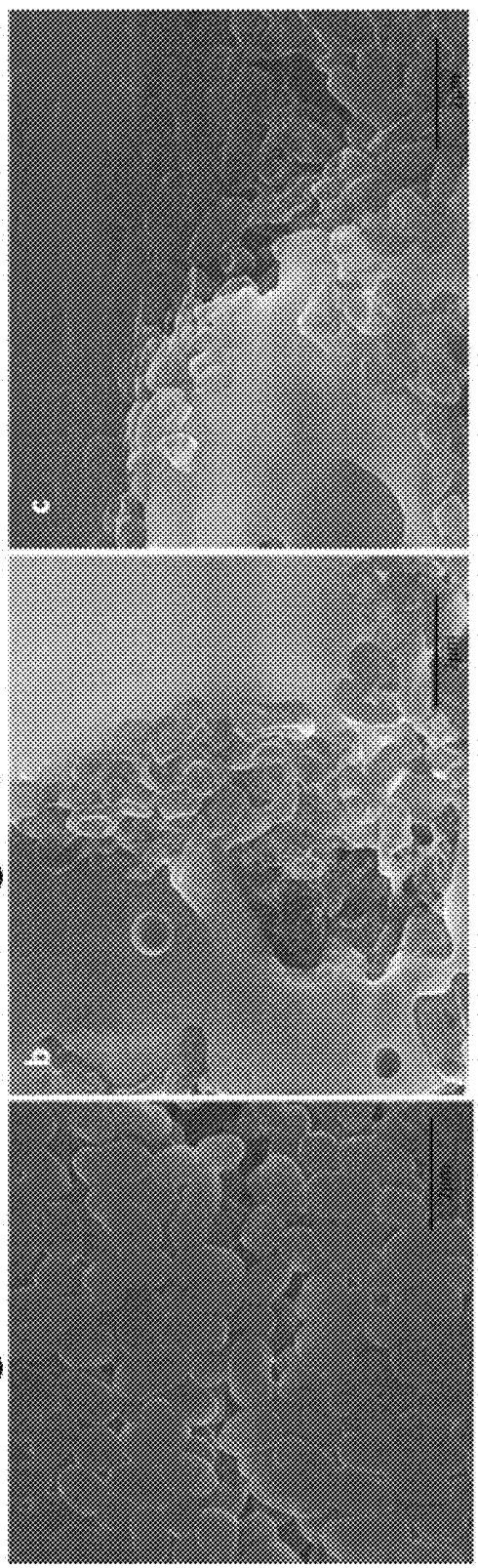
FIG. 7A. SEM micrograph of control (untreated) *E. coli* cells.
FIG. 7B. SEM micrograph of *E. coli* cells treated with *Fomes fomentarius* AgNPs at 100 μg/mL.
FIG. 7C. SEM micrograph of *E. coli* cells treated with *Fomes fomentarius* $TiO_2NPs$ at 100 μg/mL.

Topological changes caused by the synthesized NPs in *E. coli* and *S. aureus* were further evaluated by SEM. The untreated (control) *E. coli* cells appeared to be rod-shaped, having a consistent and intact cell surface (FIG. 7A). However, treated *E. coli* cells were no longer intact, with abnormal and irregular appearance at the cellular surfaces (FIG. 7B). The cells treated with AgNPs appeared more affected than those of the TiO$_2$ NPs (FIG. 7C).

The *E. coli* cells treated with TiO$_2$ NPs showed mild alteration, whereas *E. coli* cells were severely damaged by AgNPs. While not being bound to a particular explanation, the inventors consider that this was attributable to pit formation and distortion of cellular wall and membrane, reflecting the loss of the cellular integrity, and leading to bacterial death.

On the other hand, the control cells (untreated) *S. aureus* cells were found in normal coccus shape, with a smooth and continuous cell surface (FIG. 8A). Contrary to this, the treated *S. aureus* cells were irregular in shape and had a distorted cell surface. Both AgNPs and TiO$_2$ NPs, had similar effects on Gram-positive cells. The cell surface was seen as irregular with a distorted cellular surface. The obtained results suggested that the *E. coli* cells were more severally affected as compared to *S. aureus*, when treated with AgNPs (FIGS. 8B and 8C). These results demonstrated the significant activity of AgNPs. Such properties of AgNPs may be employed for development of effective antibacterial compositions or for application in food packaging materials and other durable polymeric materials.

Anticancer Activity of Synthesized NPs. The impact of biosynthesized NPs was examined for microscopic observations and by an MTT cell proliferation assay. Both TiO$_2$ and AgNPs showed dose-dependent effects on cancer cell survivability as examined by MTT assay.

Figure 9B:
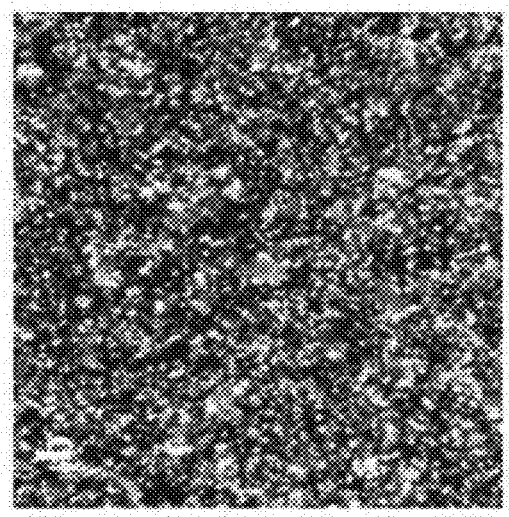
FIG. 9B. Cell morphology of HCT 116 cells treated with treated with 8.0 μg/mL *Fomes fomentarius* AgNPs by light microscopy.
Figure 9D:
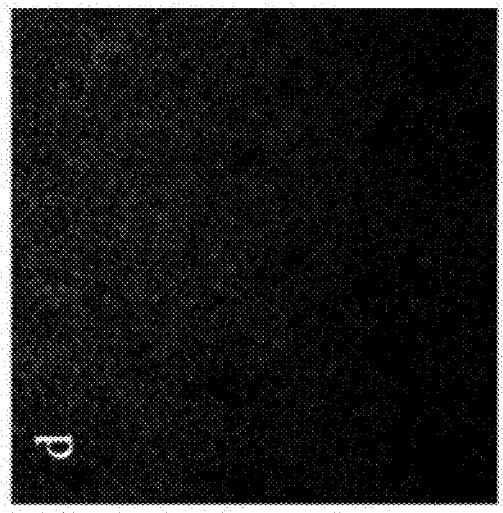
FIG. 9D. Cell morphology of HCT 116 cells treated with treated with 8.0 μg/mL *Fomes fomentarius* AgNPs by confocal scanning microscopy.
Figure 9A:
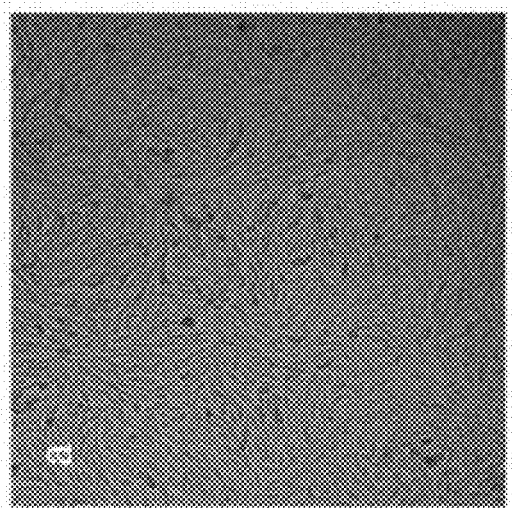
FIG. 9A. Cell morphology of HCT 116 cells (control) by light microscopy.

The treatment of AgNPs also showed strong cytotoxic effects on cancer cell viability, as a larger majority of the cells were found dead after treatments of lower than 0.5 μg/mL (FIG. 9A).

The treatment exhibited significant alterations in cell morphology and the cell nucleus, as revealed by DAPI staining. Clear evidence of condensation and disintegration of the nucleus was seen, with lots of cancer cells found dead during the observation. NP treatment caused significant loss of nuclear staining as compared to control cells (FIG. 9B). Data represented are the means±SD of three replicated experiments. No significant damage was found in the control group.

The impact of biosynthesized NPs on cancer cells was microscopically examined and examined using an MTT assay. Both TiO$_2$ and AgNPs produced dose-dependent effects on cancer cell survivability as shown by the MTT assay. Treatment of cancer cells with AgNPs also produced strong cytotoxic effects on cancer cell viability as a larger majority of the cells were found dead after treatments of lower than 0.5 μg/mL (FIG. 9E).

Figure 9C:
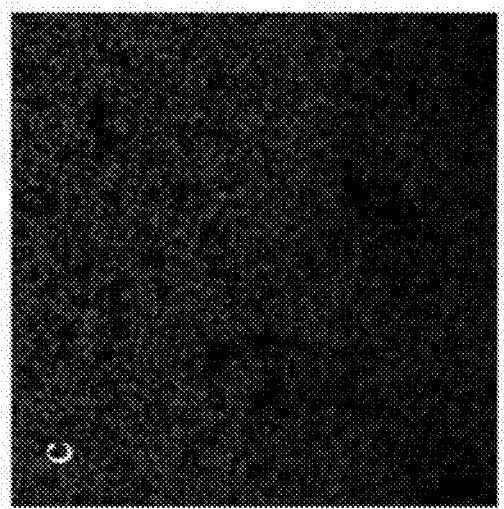
FIG. 9C. Cell morphology of HCT 116 cells (control) by confocal scanning microscopy.

Treatment with *Fomes fomentarius* nanoparticles produced significant alterations in cell morphology and in the cell nucleus as revealed by DAPI staining. Clear evidence of condensation and disintegration of the nucleus was seen and a large proportion of the cancer cells were dead. NP treatment caused significant loss of nuclear staining (FIGS. 9B and 9D) as compared to control cells (FIGS. 9A and 9C). Data represented are the means±SD of three replicated experiments. No significant damage was found in the control group.

Figure 10B:
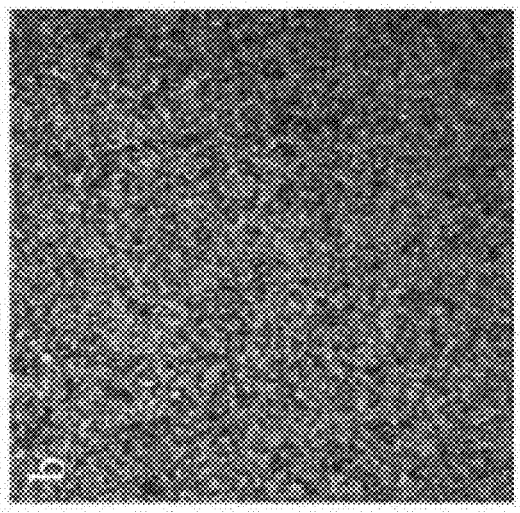
FIG. 10B. Cell morphology of HCT 116 cells (treated with treated with 8.0 μg/mL *Fomes fomentarius* AgNPs by light microscopy.
Figure 10D:
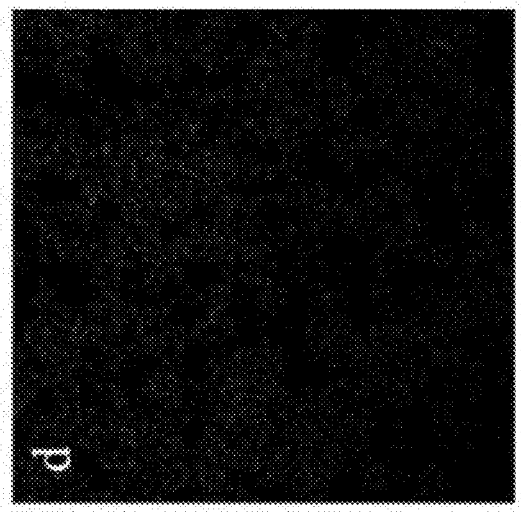
FIG. 10D. Cell morphology of HCT 116 cells treated with treated with 8.0 μg/mL *Fomes fomentarius* AgNPs by confocal scanning microscopy.
Figure 10A:
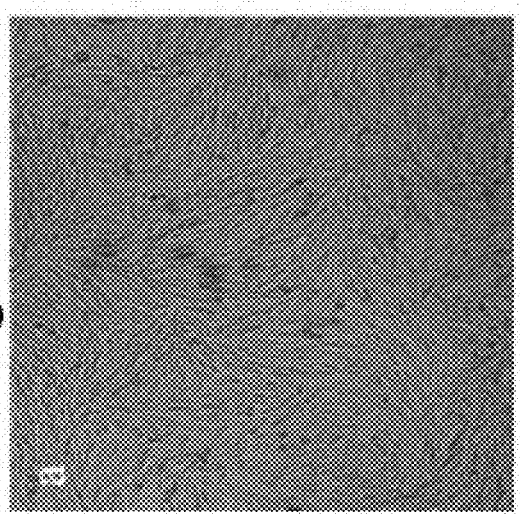
FIG. 10A. Cell morphology of HCT 116 cells (control) by light microscopy.
Figure 10C:
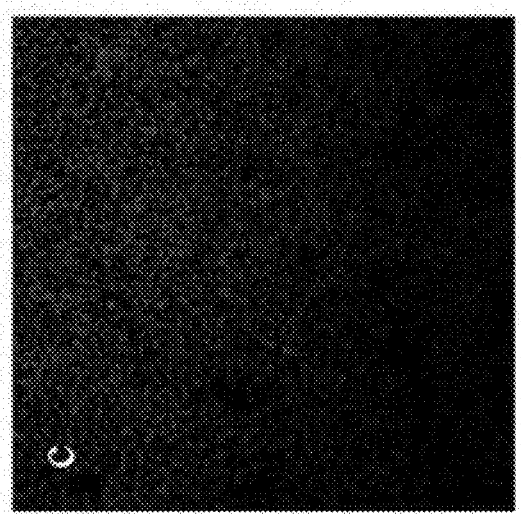
FIG. 10C. Cell morphology of HCT 116 cells (control) by confocal scanning microscopy.
Figure 10E:
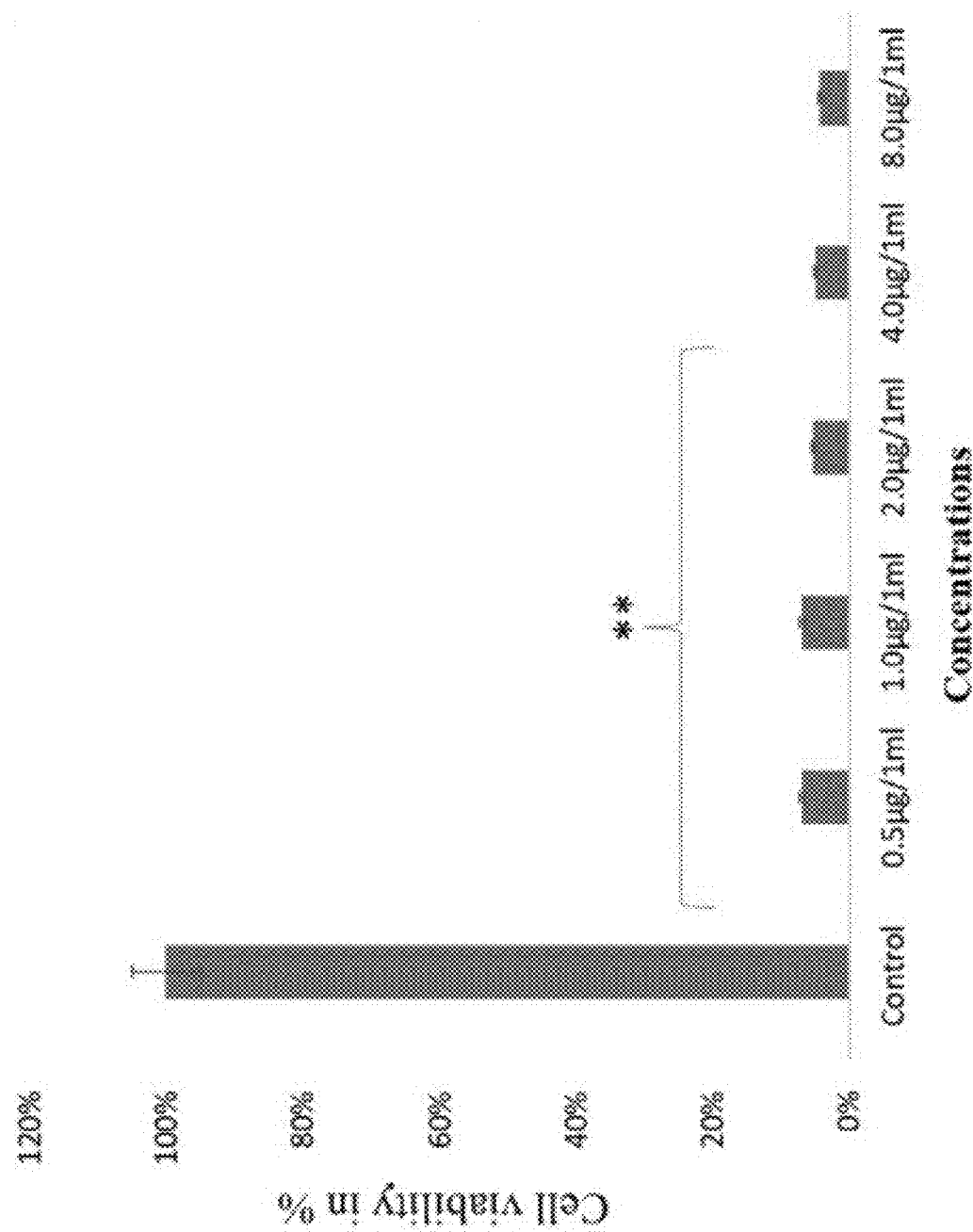
FIG. 10E. Cell viability by MTT Assay. The HCT-116 cells treated with different concentrations of *Fomes fomentarius* $TiO_2NPs$ after 48 h. Differences between two treatment groups were analyzed by student's t test where ** $p<0.01$.

Treatment with $TiO_2$ NPs also produced strong cytotoxic effects on cancer cell viability and a large majority of the cells were found dead after treatments of lower than 0.5 µg/mL (FIG. 10E). Significant changes in cell structure and nucleus were depicted by DAPI staining. The nuclear disintegration and condensation were indicated with many dead cells seen (FIGS. 10B and 10D). Control cells were found unaffected during treatment (FIGS. 10A and 10C).

Example 2

Nanoparticles Made with *Fomitopsis pinicola*

This example describes a bio-directed approach for the formation of titanium oxide and silver nanoparticles ($TiO_2$ and AgNPs), using a wild mushroom, *Fomitopsis pinicola*, identified by 18S ribosomal RNA gene sequencing (gene accession no. MK635350) and phenotypic examination.

NP synthesis was confirmed by X-ray diffraction (XRD), Fourier transform infrared spectroscopy (FT-IR), diffuse reflectance UV-visible spectroscopy (DR-UV), and scanning and transmission electron microscopy (SEM/TEM). Furthermore, the impact of NPs on *Escherichia coli* and *Staphylococcus aureus* and a human colon cancer cell line (HCT) were evaluated by MIC/MBC and MTT assays, respectively, along with structural morphogenesis by different microscopy methods. The results showed that *Fomitopsis pinicola* $TiO_2$ and AgNPs were significantly active, and that enhanced antibacterial and anticancer action was seen with AgNPs having average diameters ranging from 10-30 nm. Such NPs can be utilized to control and treat infectious diseases and colon cancer and therefore have potential in a range of biomedical applications.

Collection, phenotypic and genotypic studies of *F. pinicola*. For the collection of sporocarps, standard method was followed; see D. Krueger, *Monographic studies in the genus Polyporus (Basidiomycotina)*, 2002, incorporated by reference.

Photographs were taken by Nikon D5300 DSLR Camera with a zoom lens of 18-140 VR. Passport data and the micro-habitat characteristics of collected sample were written in the field book. Each sample was properly labeled, given a voucher number and, carried to a laboratory for detailed morphometric examination. Collected specimens were identified by keen observation of structures like pileus, stipe, their shape, structure, gill attachment, etc., using standard keys (e.g., Mycokey, Index fungorum, etc.) field guides and manuals. The samples were dried and deposited at the herbarium of the Centre for Biodiversity and Taxonomy, University of Kashmir, J&K, India.

Microscopic features and measurements were made from slides prepared and stained with lactophenol cotton blue, 2% KOH and Melzer's reagent. For spore examination, the spores were tapped off a razor blade onto a clean slide and a drop of KOH or Melzer's reagent was added. Observation and photographs were captured at a magnification between 40× to 100×, using a Nikon Eclipse 80i microscope and phase contrast illumination (Nikon, Tokyo).

DNA isolation and PCRDNA extraction was done using manual CTAB method (cetyltrimethylammonium bromide); S. Rehman, et al., *Comparative studies and identification of camptothecin produced by an endophyte at shake flask and bioreactor*, NAT. PROD. RES., 2009, 23(11), 1050-1057, incorporated by reference.

The extracted DNA was dissolved and preserved in TE (Tris-EDTA) buffer. The DNA was amplified for internal transcribed spacer (ITS) regions using the ITS1 and ITS4 in a PCR System Thermocycler Applied Biosystems with following parameters; denaturation for 10 min at 95° C., 35 cycles at 95° C. for 1 min, 54° C. for 30 s and 72° C. for 2 min, followed by extension at 72° C. for 10 min. The purification of amplified products was done and sequenced with the same primers; Rehman, et al., supra, incorporated by reference.

Sequence and phylogeny analysis. The small subunit sequences were aligned with additional sequences downloaded from NCBI GenBank (hypertext transfer protocol: II ncbi.nim.nih.gov) using BioEdit Sequence Alignment Editor (version 7.2.5); P. Dresch, et al., *Fungal strain matters: colony growth and bioactivity of the European medicinal polypores Fomes fomentarius, Fomitopsis pinicola and Piptoporus betulinus*, AMB EXPRESS, 2015, 5(1), 4, incorporated by reference. The sequence alignments and phylogenetic analysis were performed using MEGA 10 software (Tamura et al. 2011). Phylogeny was studied on ITS-18S rRNA genes in maximum likelihood method. Initial alignment was done using Clustal W software for maximum alignment and minimum gaps. The tree was generated by using the program DNADIST and NEIGHBOR from PHYLIP 3.69.17.

Figure 11:
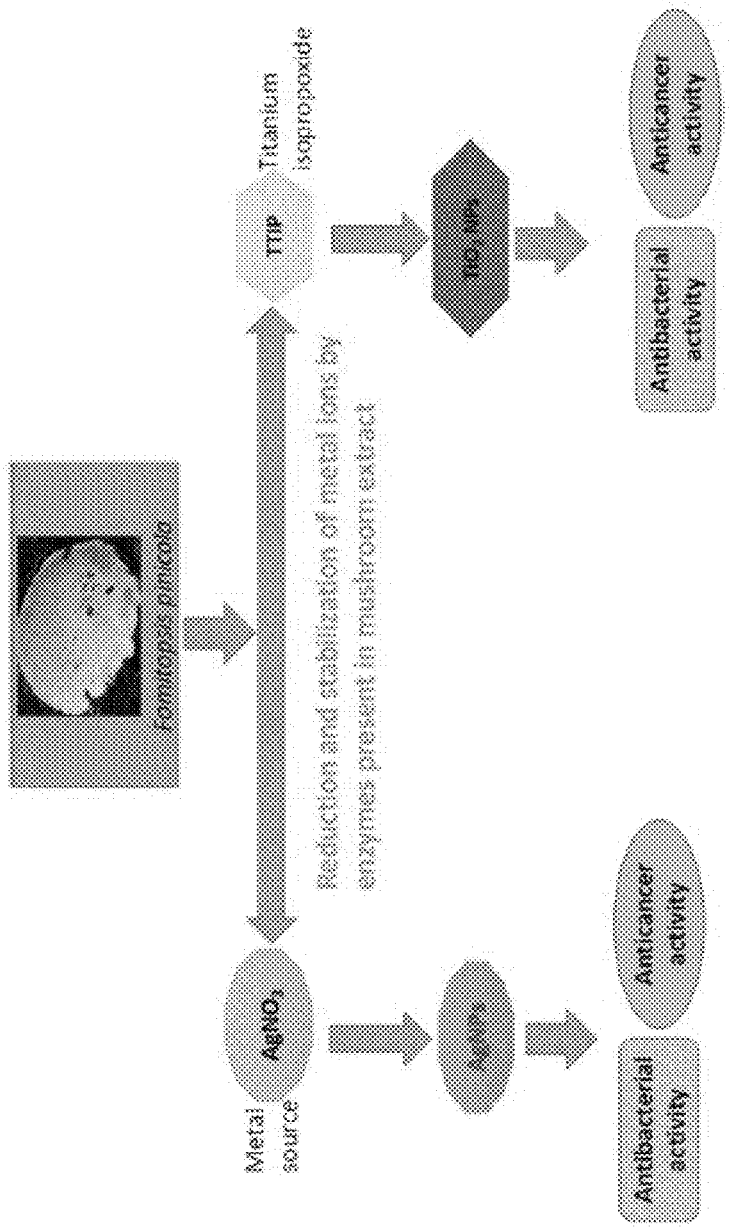
FIG. 11 schematically depicts biosynthesis of *F. pinicola* $TiO_2$ and AgNPs using an extract of *F. pinicola*.

Biosynthesis of $TiO_2$ and AgNPs using *F. pinicola*. The synthesis of $TiO_2$ and AgNPs was conducted using an extract of *F. pinicola* by adopting a green synthesis method; see Y. Mohanta, et al., *Silver nanoparticles synthesized using wild mushroom show potential antimicrobial activities against food borne pathogens*, MOLECULES, 2018, 23(3), 655, incorporated by reference. See also FIG. 11.

The samples were dried to obtain powder (10 g), which was further mixed with 100 mL of Millipore water and sonicated for 25-30 min. The sonicated mixture was centrifuged at the rpm of 4000 to obtain the clarified solution. Subsequently, the solution was filtered and stored at 4° C. 10 mL of filtrate was mixed with 1 mM $AgNO_3$ (100 mL) and put at room temperature on a shaker for agitation under observation, until the appearance of color change; Mohanta, et al., supra, incorporated by reference.

A similar procedure was followed for $TiO_2$ NPs, where 100 mL of 1 mM of titanium(IV) isopropoxide was used as source solution (Scheme 1). The mushroom extract to 1 mM $AgNO_3$ or $Ti(OC_3H_7)_4$ ratio used for the study was 1:10. Finally, the obtained NPs were filtered using Whatman filter paper, washed two times in ethanolic solution and centrifuged (4000 rpm) at 10° C. for 10 min. After drying, the sample was used for further studies.

Characterization of biosynthesized $TiO_2$ and AgNPs. The crystalline phase of $TiO_2$ and AgNPs was measured using benchtop X-ray diffractometer MiniFlex 600 (Rigaku, Japan).

The coordination environment of $TiO_2$ and AgNPs were analyzed using diffuse reflectance UV-visible spectroscopy (V-750, JASCO).

The $TiO_2$ and AgNPs functional groups were analyzed using Fourier transform infrared spectroscopy (PerkinElmer).

The surface morphology, distribution and features of $TiO_2$ and AgNPs were studied using SEM (Inspect S50) and TEM (Morgagni 268). For TEM analysis, samples were prepared by dispersing in ethanol followed by shaking in an ultrasonicator for 20 min, and then a suspended drop was dried at room temperature on the carbon-coated copper grid; see S. Rehman, et al., *Isolation and characterization of a novel thermophile; Bacillus haynesii, applied for the green synthesis of ZnO nanoparticles*, ARTIF. CELLS, NANOMED., BIOTECHNOL., 2019, 47(1), 2072-2082, incorporated by reference.

Antibacterial activity of biosynthesized NPs. Antibacterial activities of synthesized, $TiO_2$NPs and AgNPs were studied against the human pathogenic Gram-negative bacteria and Gram positive bacteria, namely, *E. coli* ATCC35218 and *S. aureus* ATCC29213, respectively, by broth dilution method. The bacterial strains were maintained and nutrient agar media (NA).

In preparation for the study, a homogeneous suspension of NPs was prepared by sonication for 15-20 min at 30° C., ranging in the concentration from 250 to 15.62 mg $mL^{-1}$. Mueller-Hinton (MHB) was used to grow test organisms for overnight at 37° C. and subsequently adjusted to the cell frequency of 106 $CFUmL^{-1}$.

The adjusted inoculum of each bacterial strain was added to the solution of MHB with NPs and incubated with shaking at 37° C. for 24 h. Untreated bacteria was used as a negative control.

The MIC was recorded as the least concentration of NPs, which had no growth visible in the broth (absence of turbidity). Following the MIC evaluation, MBC was obtained by taking an aliquot of the MIC for further plating on the MHA plates. The inoculated plates were further incubated for overnight at 37° C. and the MBC was taken as the concentration at which no growth or CFU less than 3 was obtained; see S. Akhtar, et al., *Synthesis of $Mn_{0.5}Zn_{0.5}Sm_xEu_xFe_{18-2x}O_4$ Nanoparticles via the Hydrothermal Approach Induced Anti-Cancer and Anti-Bacterial Activities*, NANOMATERIALS, 2019, 9(11), 163, incorporated by reference.

Study of topological changes in treated bacteria. Additionally, the treated cultures of *E. coli* and *S. aureus* were studied by SEM for the morphological and physiological alteration caused by exposure to NPs. Precisely, adjusted bacterial cells were treated at the concentration obtained as its MIC and subjected to incubation at 37° C. for overnight. Untreated samples were included as the negative control. Later treated and untreated cells were centrifuged at 12 000 rpm for 10 min. The harvested cells were thrice washed using PBS and primarily fixed using 2.5% glutaraldehyde for 4 h, then again fixed with 1% osmium tetroxide for 1-2 h. Cells were washed multiple times and further dehydrated by varying conc. of ethanol (50%, 70%, 90%, 100%). The cells were placed on aluminum stubs and dried using desecrator. Finally, gold coating was done and cells were examined by SEM at an accelerating voltage of 20 kV; see Akhtar, et al., supra, incorporated by reference.

Antiproliferative activity: Cell culture & treatments. Human colorectal carcinoma cells (HCT-116) were used for the study. DMEM medium was used for cell culture which was supplemented with 10% fetal bovine serum (FBS); (10%) L-glutamine; 10% selenium chloride; 120 mg $mL^{-1}$ and streptomycin; and 120 units per mL penicillin in 5% CO2 incubator (Thermo Scientific Heracell-150) at temperature 37° C. The cells with more than 70-80% confluence were used for the $TiO_2$ and AgNPs treatments.

The treatments of HCT-116 cells were carried out with different concentrations of nanoparticles ranging from 0.5 to 8.0 mg $mL^{-1}$. The cells were observed after the time span of 48 h. Experiments were carried out in triplicate for statistical analysis; see F. Khan, et al., *FMSP-nanoparticles induced cell death on human breast adenocarcinoma cell line (MCF-7 cells): morphometric analysis*, BIOMOLECULES, 2018, 8(2), 32, incorporated by reference.

Cancer cell morphology. The cell morphology of untreated and treated HCT-116 cells was examined post 48 h under inverted microscope (TS100E-Eclipse, Nikon) and compared the under 200× magnifications.

Cytotoxicity by MTT assay. The cells with confluency of 70-80% in 96-well cell culture plates were subjected to MTT assay. After 48 h, MTT (5 mg mL_1) was added in all the wells and kept for 4 h. Later, DMSO was added and plate was read in an ELISA Plate Reader 570 nm wavelength (Biotek Instruments, USA). 20 The (%) percentage of cell viability was calculated as per given formula:

% cell viability=(optical density of nanoparticles)/(optical density of controls)×100.

Nuclear staining by DAPI. The cells were stained with DAPI staining to study the effects of exposure to $TiO_2$NPs and AgNPs on the cell nucleus. After 48 h, the treated and untreated HCT-116 cells were immersed in an ice-cold (4%) paraformaldehyde. Later, the cells were added with Triton X-100 prepared in PBS for 5 min to premetallize the cell membrane. The cells were stained using DAPI (5 mg $mL^{-1}$) in PBS, prepared in dark. Washing with Triton X-100 was done, followed by examining the nuclear morphology under confocal scanning microscope (Zeiss, Germany) equipped with digital camera; see F. Khan, et al., *FMSP-nanoparticles induced CELL DEATH ON HUMAN BREAST ADENOCARCINOMA CELL LINE (MCF-7 CELLS)*: MORPHOMETRIC ANALYSIS, BIOMOLECULES, 2018, 8(2), 32, incorporated by reference.

In the present study, cell viability data were presented as mean (±) standard deviation (SD) which were obtained from three independent experimental repeats. One-way ANOVA followed by Dunnett's post hoc test with GraphPad Prism software GraphPad Software, Inc., La Jolla, CA, USA) for the statistical analysis. $P<0.05$ was considered to indicate a statistically significant difference.

TABLE 2

Gene bank accession numbers and top BLAST match sequences of the mushroom isolated along with maximum identity, query coverage.

| Accession number | BLAST Match Sequence Reference accession number | Coverage | Maximum identity |
|---|---|---|---|
| MK635350 | MH860248.1 *Fomitopis pinicola* | 100% | 100% |
| | KC422604.1 *Boletus reticulatus* | 99% | 98.75% |
| | DQ131609.1 *Boletus aestivalis* | 99% | 98.75% |
| | DQ990837.1 Uncultured mycorrhiza | 98% | 98.99% |
| | KY595992.1 *Boletus reticulatus* | 91% | 99.18% |
| | AY680963.1 *Boletus aestivalis* | 89% | 98.88% |
| | KC261839.1 *Boletus reticulatus* | 71% | 99.47% |

The term *Fomitopsis pinicola* as used herein describes the strain deposited under MK635350 as well as phenotypically related strains, such as those described in Table 2 or those having a maximum identity of at least 98.5, 90.6, 98.7, 98.8, 98.9%, preferably at least 99.0, 99.1, 99.2, 99.3, 99.4, 99.5, 99.6, 99.7, 99.8, 99.9 or 100%, or a maximum coverage of at least 98, 99 or 100%.

Figure 12B:
FIG. 12B. Photo of *F. pinicola* basidiospores at 40×.
Figure 12A:
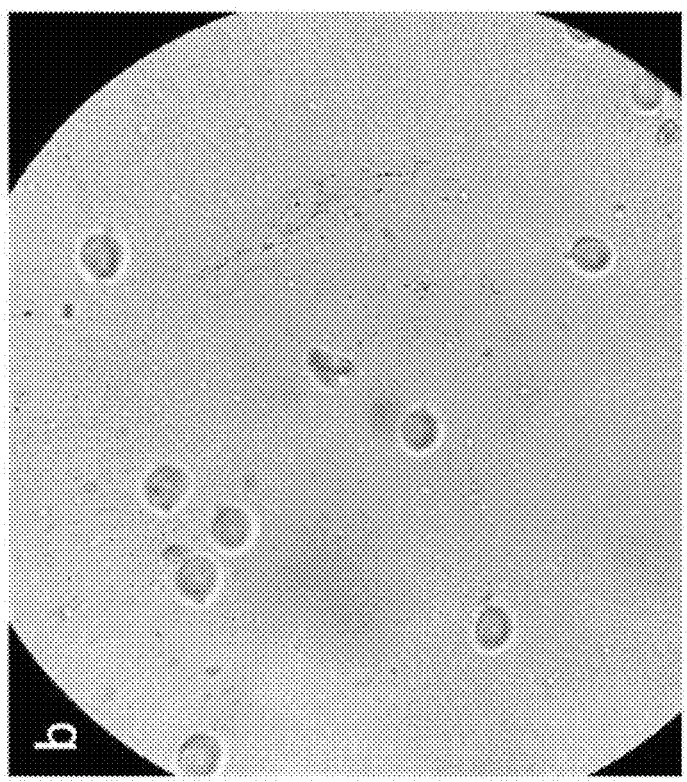
FIG. 12A is a photograph of brown rot basidiomycetes: *F. pinicola* under view showing pores.
Figure 13:
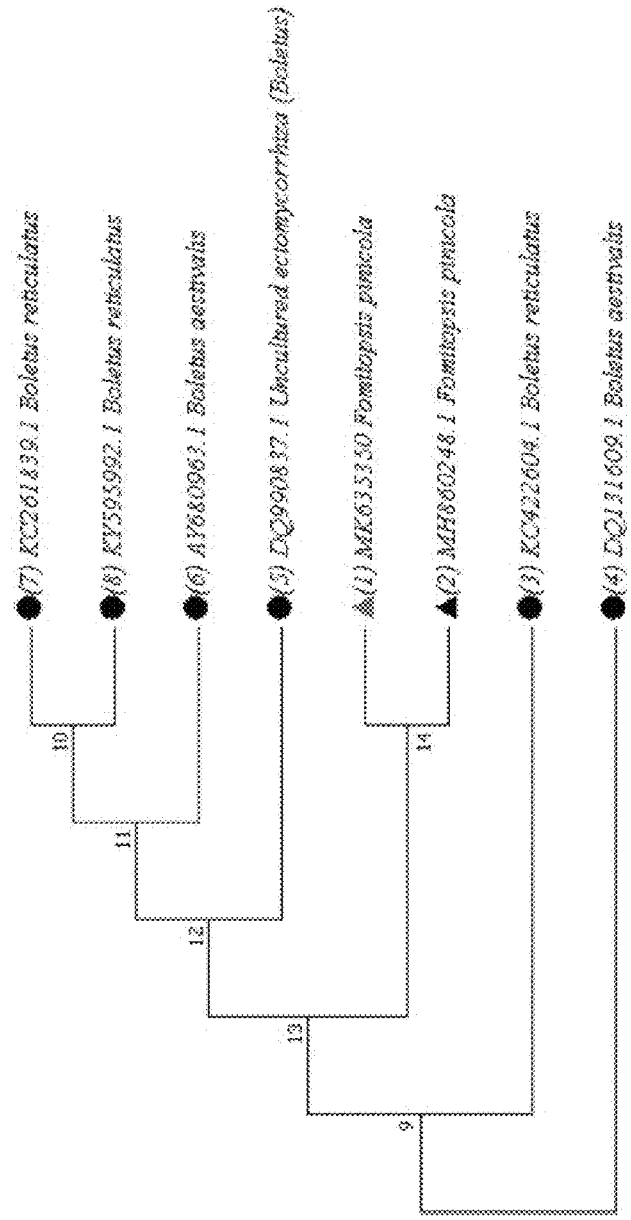
FIG. 13 describes a phylogenetic tree of *F. pinicola* indicated as A.

Phenotypic and genotypic studies of *F. pinicola*. The phenotypic analysis of mushroom namely *F. pinicola* was done. Spores are 5.5-7×4.0-5.0 μm, oval, smooth: spore print pale yellow. Spores are bilaterally symmetrical. The shape of the hilar appendix is beaked (FIGS. 12A and 12B. This was further confirmed by phylogenetic analysis of the ITS1-ITS4 sequences of the mushroom, which was deposited in the NCBI Gene Bank under accession number MK635350. The phylogenetic relationships with related species have been shown in FIG. 13.

Figure 14:
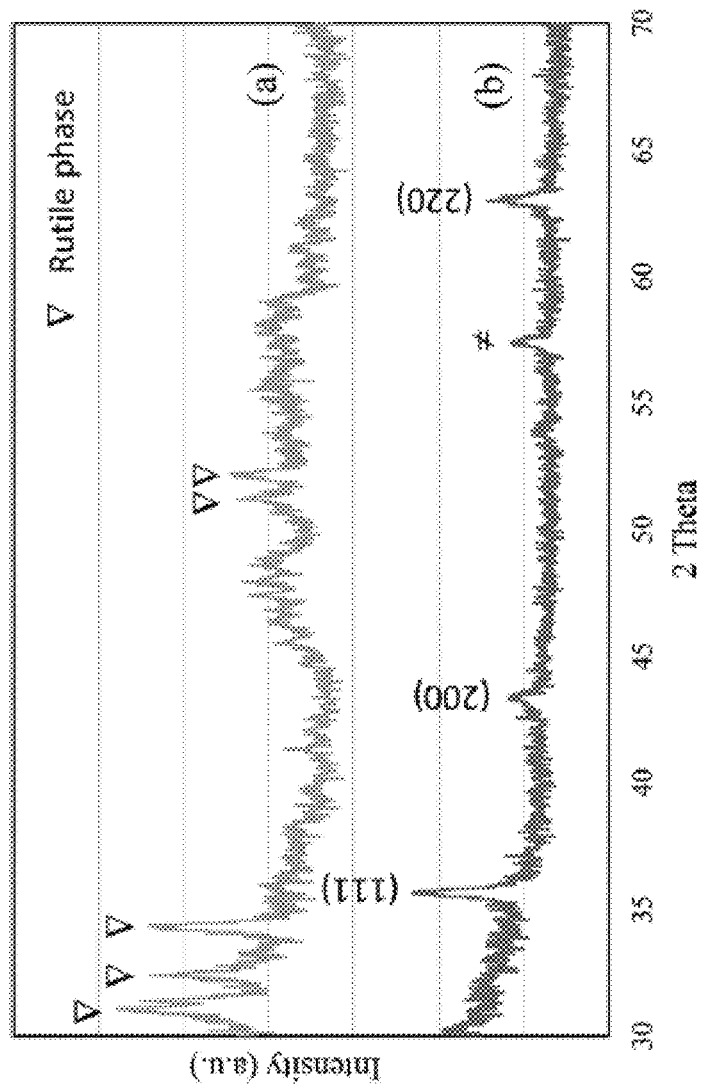
FIG. 14 is a graph illustrating the X-ray diffraction spectra of *F. pinicola* (a) $TiO_2$ and (b) AgNPs.

Characterization of biosynthesized $TiO_2$ and AgNPs. The production of *F. pinicola* $TiO_2$ and AgNPs was indicated by examining the color change in the reaction mixture. FIG. 14 shows the XRD spectra of (a) $TiO_2$ and (b) AgNPs.

In the case of $TiO_2$ NP synthesis using *F. pinicola* a reduced crystallinity and broadness of peaks indicates nano-sized $TiO_2$ formation with major phase of rutile, see FIG. 14, line a.

In the case of AgNP synthesis using *F. pinicola* the XRD spectra of AgNPs showed clear diffraction lines corresponding to (111), (200) and (220) planes indicating the presence of AgNPs; see FIG. 14, line b.

The presence of unidentified peak at about 57.5° could be attributed to the crystalline components present in the extract. While not being bound to a particular theory or explanation, the presence of active ingredients like polyphenols and flavonoids in the *F. pinicola* extract may play a role as bioreductant in reducing metal ions of metal source to nanoparticles.

Figure 15:
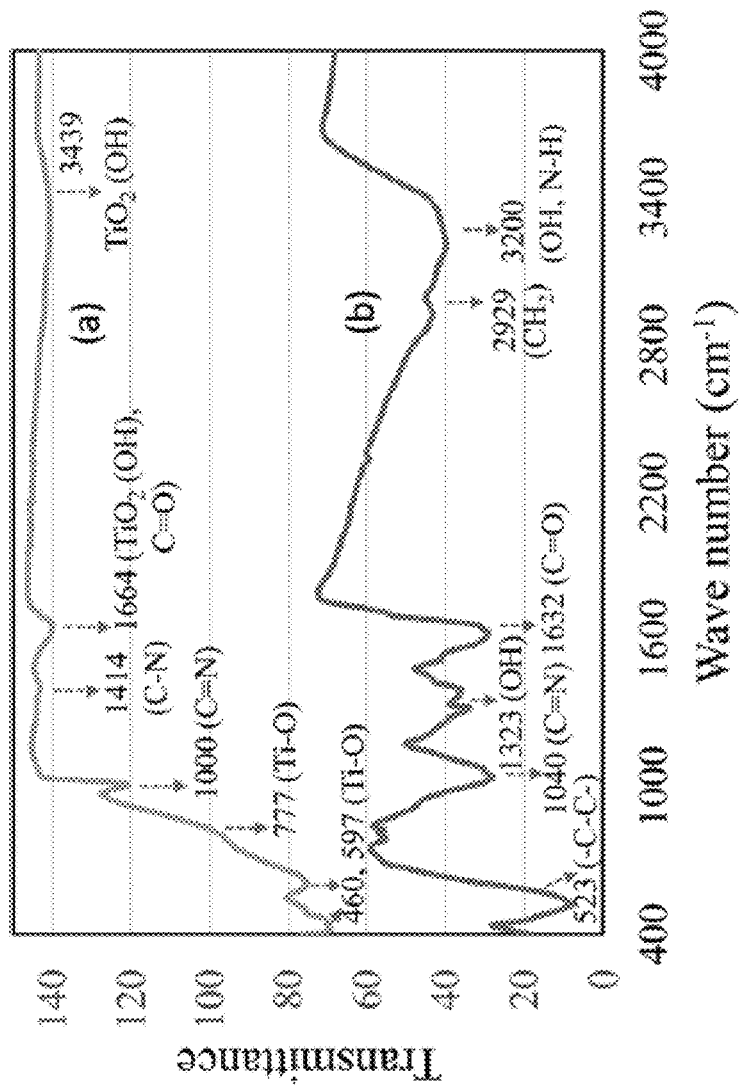
FIG. 15 is a graph illustrating the FT-IR spectra of *F. pinicola* (a) $TiO_2NPs$ and (b) AgNPs.

FIG. 15 shows the FT-IR spectroscopy of (a) $TiO_2$ and (b) AgNPs.

In the case of $TiO_2$, the hydroxyl functional group absorption coordinated TiO species was observed with distinct peaks at 1664 $cm^{-1}$ and 3480 $cm^{-1}$. The presence of $TiO_2$ was further confirmed with absorption peak of Ti—O bands at about 460, 597 and 777 $cm^{-1}$, see FIG. 15, line a.

In the case of AgNPs, presence of difference functional groups corresponding to N—H, O—H, and methylene C—H was observed between 1000-3700 $cm^{-1}$ (FIG. 15, line b). A distinct broad peak appears between 3650-2400 $cm^{-1}$ corresponding to hydroxyl (—OH), N—H stretching of primary amines and methylene ($CH_2$). The presence of asymmetrical C—O stretching peak was observed 1632 $cm^{-1}$. The presence of aromatic ring (—C—C—) and aliphatic amine (C—N) was clearly seen with an intense absorption peak at about 523 $cm^{-1}$ and 1040 $cm^{-1}$. In both cases, the presence of elongated peaks at fingerprint region between 1000-1800 $cm^{-1}$ showed several functional group moieties of mushroom extract. The linear aliphatic amines (C—N) showed peak absorption at 1000-1040 $cm^{-1}$. See FIG. 15, line b.

The functional group analysis using FT-IR suggest that active components (amino, hydroxyl and methyl) in *F. pinicola* act as bioreductants to produce $TiO_2$ and AgNPs.

The coordination sites of $TiO_2$ and AgNPs prepared using *F. pinicola* were studied using diffuse reflectance UV-visible spectroscopy.

Figure 16:
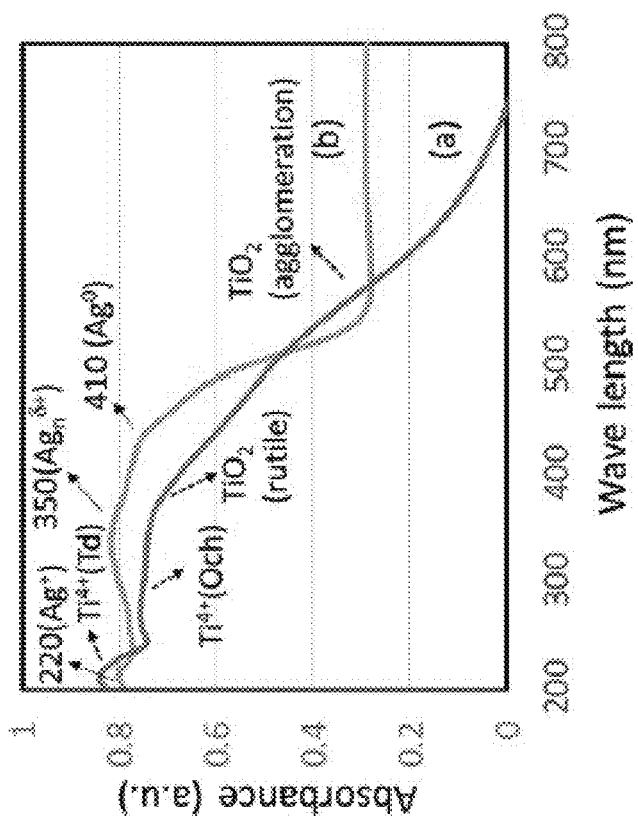
FIG. 16 is a graph illustrating the diffuse reflectance spectra of *F. pinicola* $TiO_2NPs$ (a) and AgNPs (b).

In case of $TiO_2$ NPs, isolated tetrahedral $Ti^{4+}$ species was observed with a band at about 220 nm (FIG. 16, line a). The presence of distinct peaks corresponding to rutile and octahedral Ti compounds were observed between 250-420 nm. The presence of anatase (titania) phase was also reported at about 350 nm. The result coincides with XRD analysis, which indicated the presence of rutile and anatase phase of $TiO_2$. The presence of few agglomerated $TiO_2$ species were also observed between 500-600 nm.

In case of AgNPs, the sample exhibited presence of three kinds of Ag species indicating the variation in coordination environments (FIG. 16, line b). A weak absorption at about 224 nm indicates presence of few $Ag^+$ species. However, the strong absorption at 352 nm showed presence of $Ag_n^{\delta+}$ nanoclusters as predominant species followed by Ag0 with absorption maxima ranging between 410-540 nm.

FIG. 17 shows SEM and TEM morphologies of $TiO_2$ and AgNPs.

Figure 17A:
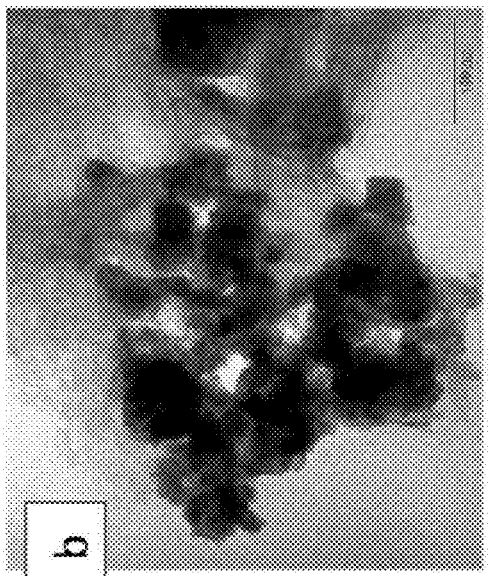
FIG. 17A. SEM of *F. pinicola* $TiO_2NPs$.
Figure 17B:
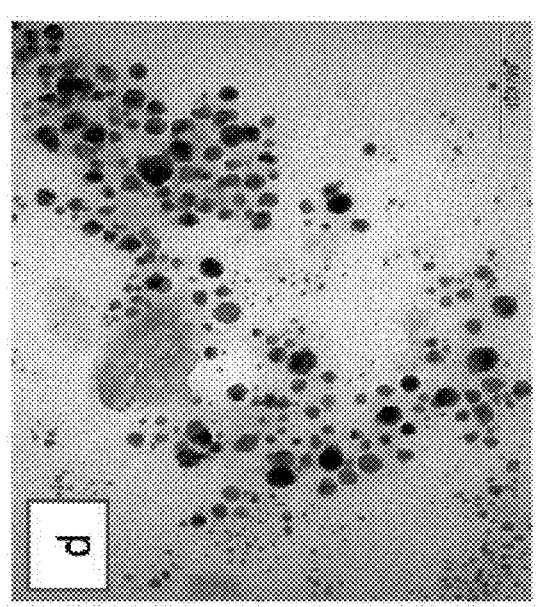
FIG. 17B. TEM image of *F. pinicola* $TiO_2NPs$.
Figure 17C:
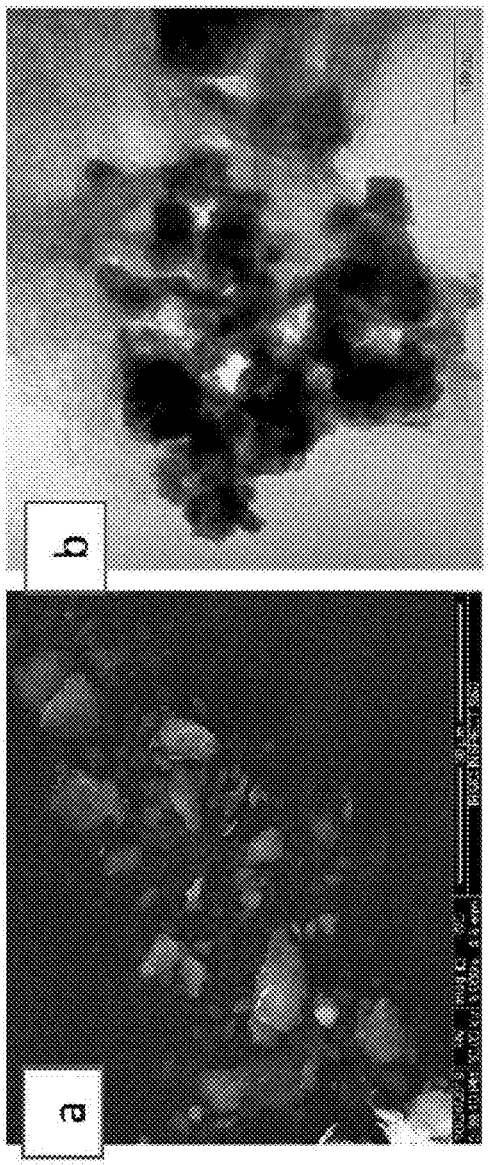
FIG. 17C. SEM of *F. pinicola* AgNPs.
Figure 17D:
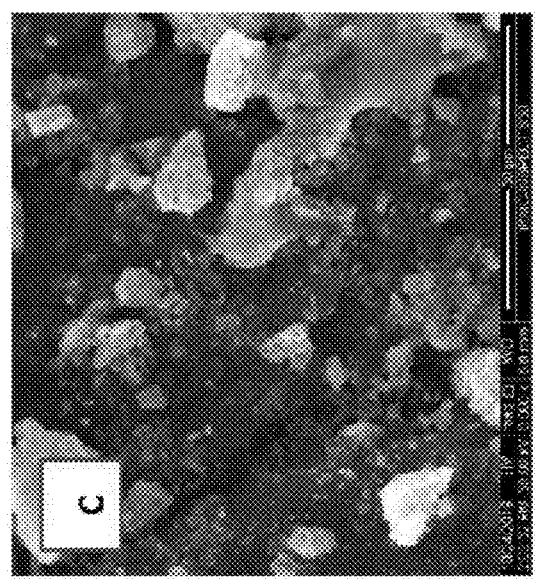
FIG. 17D. TEM image of *F. pinicola* AgNPs.

For $TiO_2$ NPs, surface features and distribution have been examined through SEM (FIG. 17A). SEM micrographs showed that these nanoparticles are dispersed in irregular distribution with rough surface. TEM micrographs (FIG. 17B) showed irregular shape and size.

For AgNPs, on the other hand, SEM micrographs (FIG. 17C) shows spherical Ag nanoparticles with some agglomeration of nanoparticles, while TEM (FIG. 17D) depicted well distribution of small spherical nanoparticles with average diameter ranging from 10-30 nm.

Antibacterial activity of synthesized NPs. Assays were performed by examining the MIC and MBC values of *F. pinicola* nanoparticles against *E. coli* and *S. aureus*. See FIG. 18E.

Figure 18A:
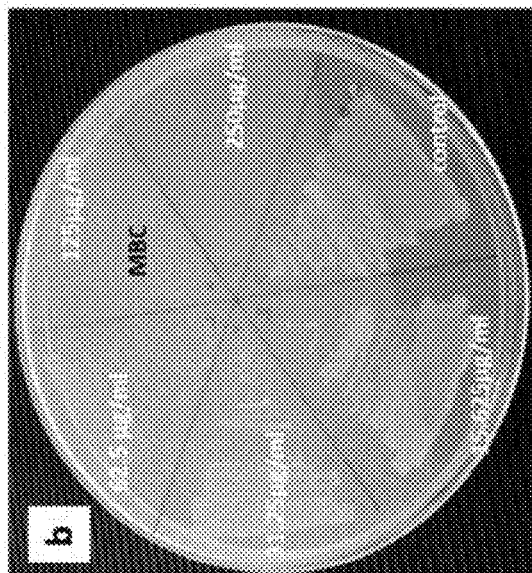
FIG. 18A shows *E. coli* treated with different concentrations of *F. pinicola* $TiO_2NPs$.
Figure 18B:
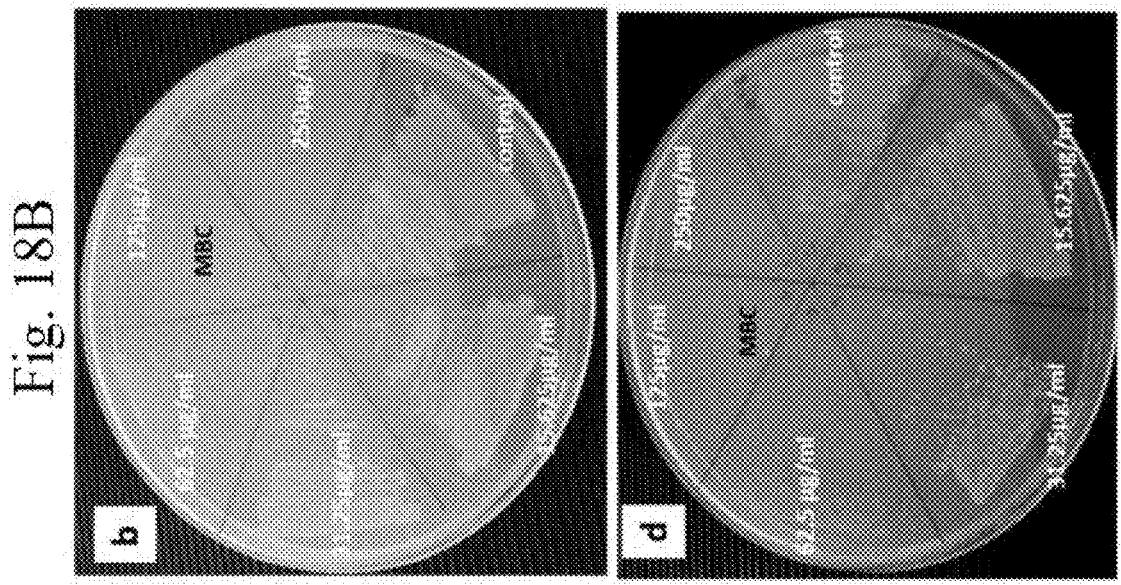
FIG. 18B shows *S. aureus* treated with different concentrations of *F. pinicola* $TiO_2NPs$.

On treatment with $TiO_2$ NPs, the MIC/MBC values were 62.5/125 and 62.5/125 mg $mL^{-1}$ for *E. coli* and *S. aureus*, respectively (FIGS. 18A and 18B).

Figure 18C:
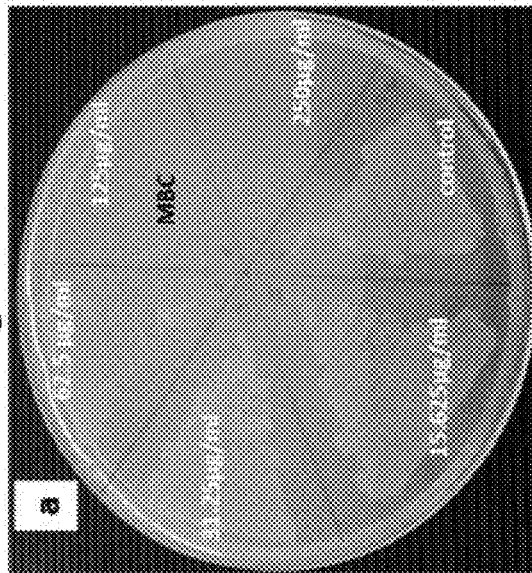
FIG. 18C shows *E. coli* treated with different concentrations of *F. pinicola* AgNPs.
Figure 18D:
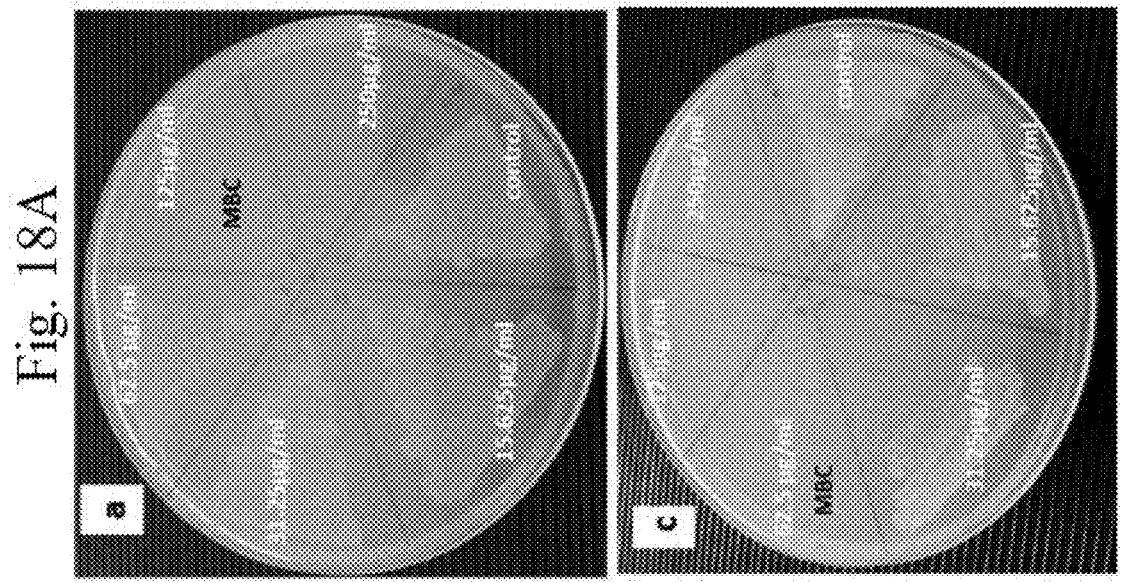
FIG. 18D shows *S. aureus* treated with different concentrations of *F. pinicola* AgNPs.
Figure 18E:
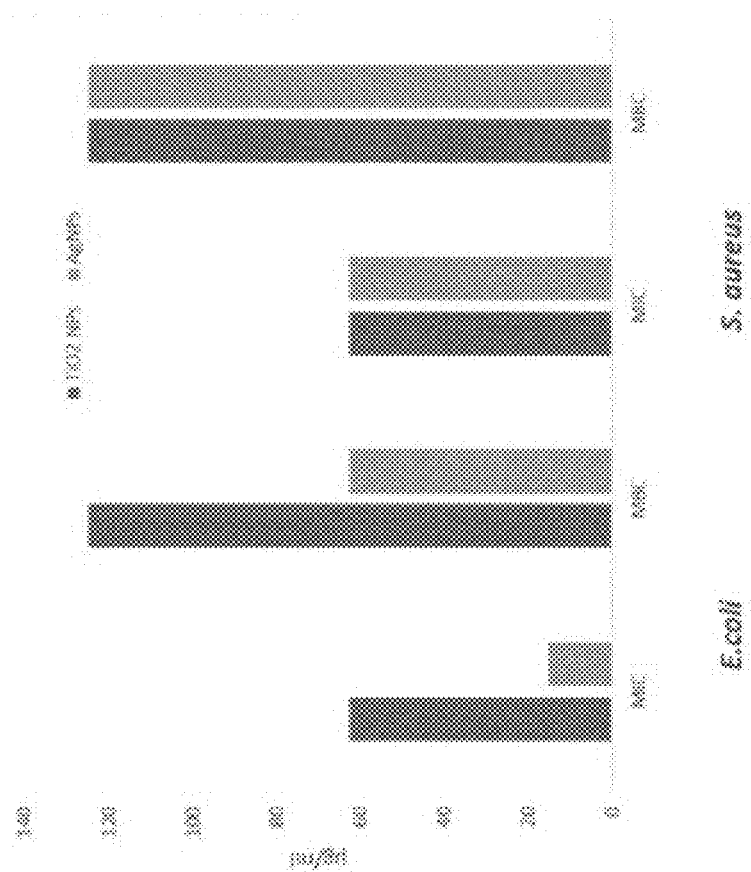
FIG. 18E. MIC/MBC assay results.

Whereas upon treatment with AgNPs, the MIC/MBC values obtained were 15.62/62.5 and 62.5/125 $mgmL^{-1}$ for *E. coli* and *S. aureus*, respectively (FIGS. 18C and 18D). Both the biosynthesized NPs were found to have a significant activity against both organisms, although enhanced activity was obtained with AgNPs against *E. coli*.

Study of topological changes in treated bacteria. Morphological changes to the tested bacteria induced by synthesized $TiO_2$ and AgNPs were further studied by SEM.

Figure 19C:
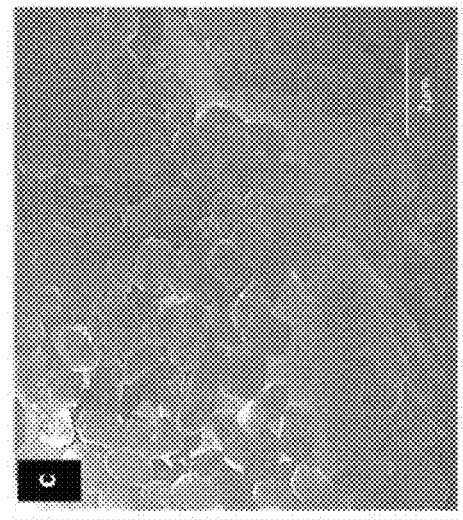
FIG. 19C shows an SEM micrograph of *E. coli* cells treated with a MIC of *F. pinicola* AgNPs.
Figure 19B:
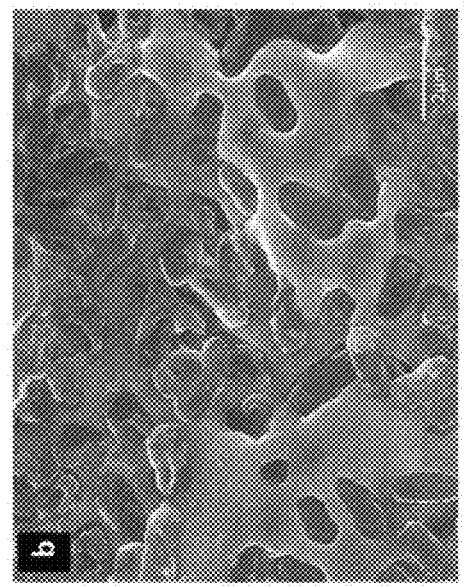
FIG. 19B shows an SEM micrograph of *E. coli* cells treated with a MIC of *F. pinicola* $TiO_2NPs$.
Figure 19A:
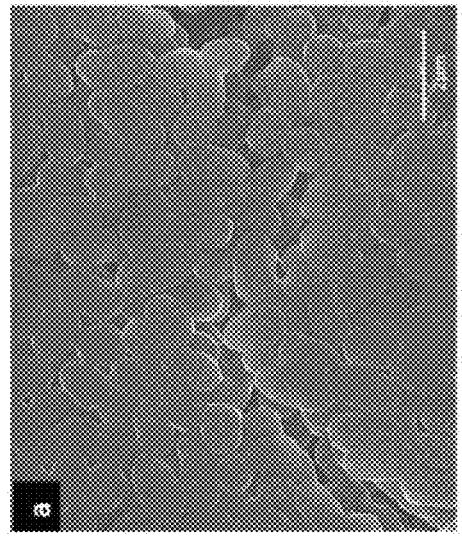
FIG. 19A shows an SEM micrograph of *E. coli* control (untreated) cells.
Figure 19F:
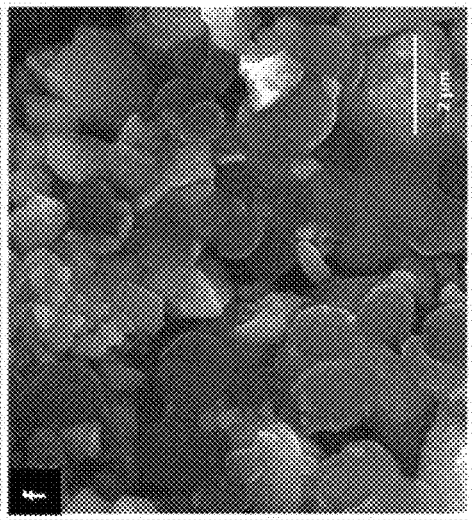
FIG. 19F shows an SEM micrograph of *S. aureus* cells treated with a MIC of *F. pinicola* AgNPs.
Figure 19E:
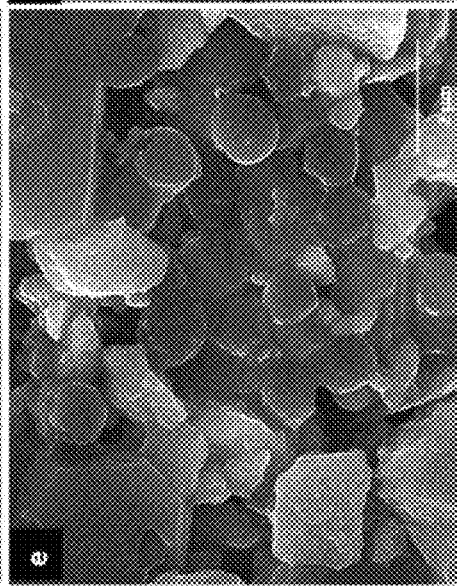
FIG. 19E shows an SEM micrograph of *S. aureus* cells treated with a MIC of *F. pinicola* $TiO_2NPs$.

The control (untreated) *E. coli* cells, appeared as normal rod-shaped cells with a consistent and smooth cell surface (FIG. 19A).

The treatment of *E. coli* cells with $TiO_2$NPs produced some structural alterations (FIG. 19B)

Although treated *E. coli* with both the NPs was not found intact, with irregularities at cell surfaces seen.

Treatment of *E. coli* with AgNPs severely affected morphology (FIG. 19C) and revealed that the AgNPs treated cells were more damaged than that of the $TiO_2$ NPs treated cells.

Figure 19D:
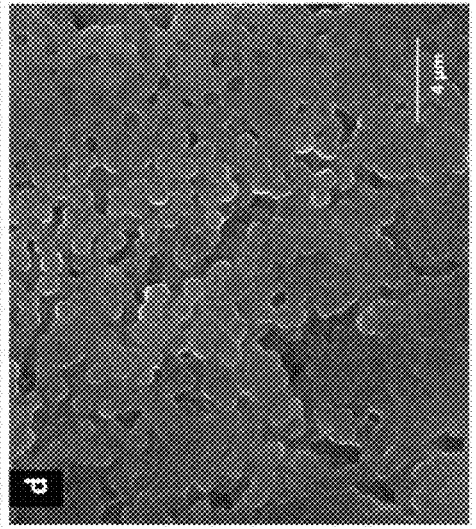
FIG. 19D shows an SEM micrograph of *S. aureus* control (untreated) cells.

Untreated *S. aureus* control cells are shown by FIG. 19D. These were normal in shape i.e., cocci with smooth cell surfaces.

On the contrary to the control cells, the treated *S. aureus* cells exhibited irregularities and distorted cell surfaces. Both the $TiO_2$ and AgNPs had similar effects on the Gram-positive bacteria.

Antiproliferative activity. The dose-depended effects of *F. pinicola* nanoparticles on cancer cells were evaluated.

Figure 20E:
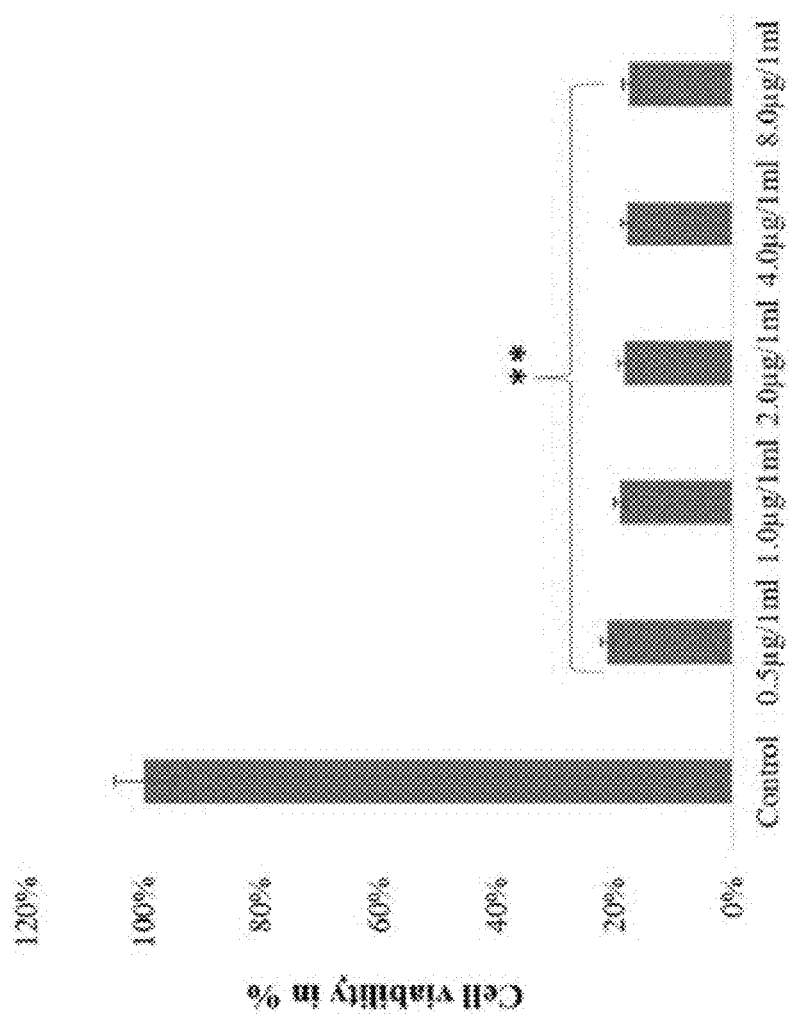
FIG. 20E shows cell viability of HCT-116 cells by MTT assay on treatment assay on treatment with $TiO_2NPs$ after 48 h. Data are the mean±SD of three different experiments. Difference between two treatment groups were analyzed by Student's t test where **$p<0.01$, p-values were calculated by Student's t-test. No changes were observed in control group.

$TiO_2$NPs showed strong cytotoxic effects on cancer cell viability as a majority of the cancer cells were found dead after treatments of lower 0.5 mg $mL^{-1}$ (FIG. 20F).

$TiO_2$NP treated cells showed significant alteration in structure and the cell nucleus as revealed by light and confocal microscopy (FIGS. 20B and 20D). It was evident that that the cancer cell nucleus had disintegrated, and a nuclear condensation was observed, along with the death of many cancer cells. $TiO_2$ NPs-treatment caused significant loss of nuclear staining in the HCT-116 cells as seen by DAPI staining as compared to control cells (FIGS. 20A and 20C).

Figure 21B:
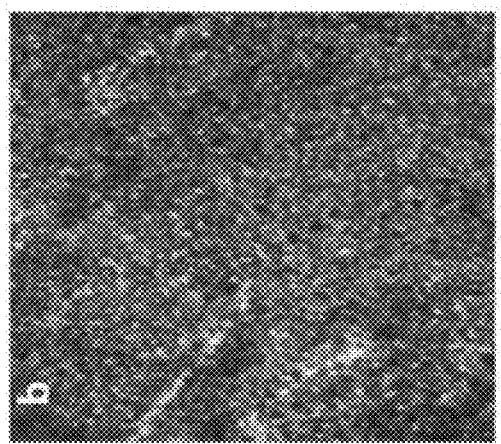
FIG. 21B. Morphology of cells treated with 8.0 µg mL$^{-1}$ of *F. pinicola* AgNPs (light microscopy).
Figure 21D:
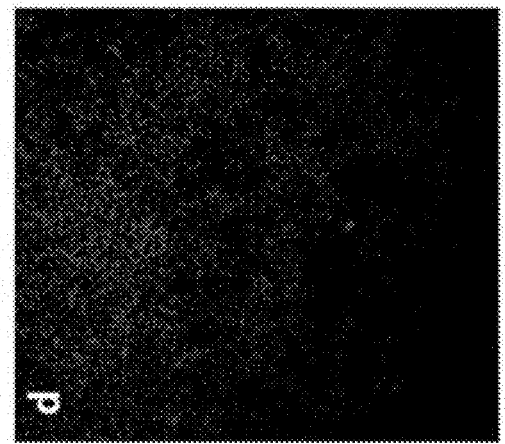
FIG. 21D. Morphology of cells treated with 8.0 µg mL$^{-1}$ of *F. pinicola* AgNPs (confocal microscopy).
Figure 21A:
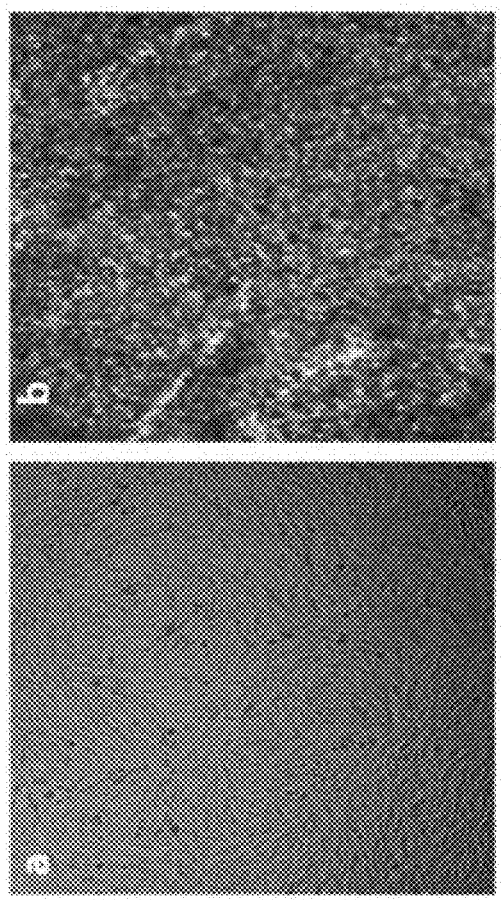
FIG. 21A. Morphology analysis of control cells (light microscopy).
Figure 21C:
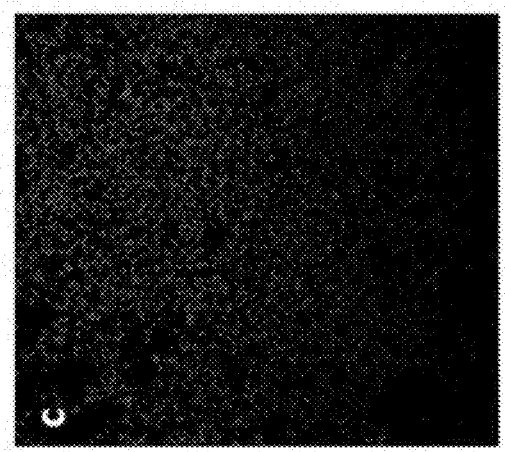
FIG. 21C. Morphology analysis of control cells (confocal microscopy).
Figure 21E:
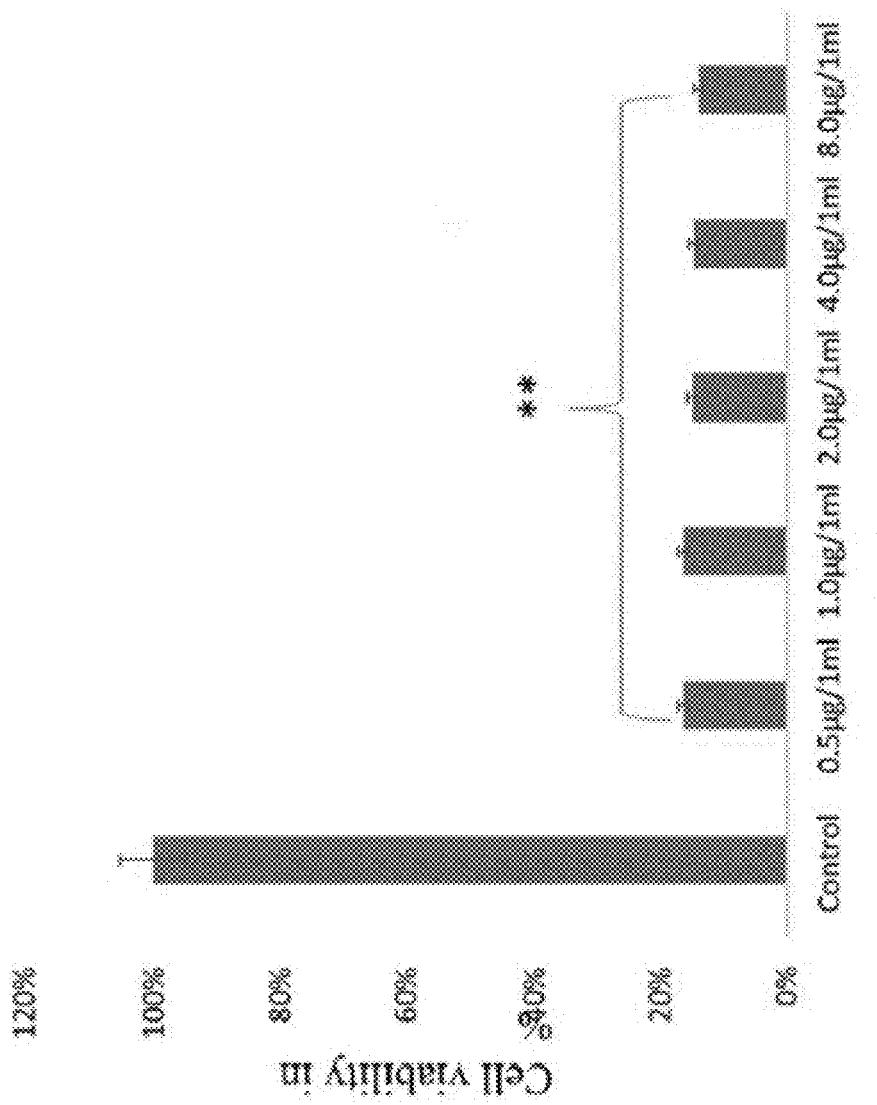
FIG. 21E illustrates cell viability of HCT-116 cells by MTT assay on treatment with AgNPs after 48 h. Data are the mean±SD of three different experiments. Difference between two treatment groups were analyzed by Student's t test where **p<0.01, p-values were calculated by Student's t-test. No changes were observed in control group.

Treatment with AgNPs also produced strong cytotoxic effects on cancer cell viability as a majority of the cells were found dead after the treatment of 0.5 mg mL-' (FIG. 21E). AgNPs produced significant deformities in cell morphology and the nucleus as revealed by light and confocal microscopy (FIGS. 21B and 21D). Clear evidence of disintegration and condensation of nucleus was observed and as many cells were found dead. Treatment with AgNPs caused significant loss of nuclear staining in the HCT-116 cells as seen by DAPI staining (FIG. 21D) with compared to control cells (FIGS. 21A and 21C).

As shown in this example, TiO$_2$NPs and AgNPs containing *Fomitopsis pinicola* exhibited antibacterial activity against both Gram-negative and Gram-positive bacteria and inhibited the growth of, or killed, cancer cells. These antimicrobial and anti-cancer properties may be applied for treatment of bacterial infections or cancer as well as in industries, such as food production and distribution, or cosmetics.

The invention claimed is:

1. A method of making TiO$_2$ nanoparticles, comprising:
   drying a *Fomitopsis pinicola* sample to form a *F. pinicola* powder,
   mixing the *F. pinicola* powder with water to form a *F. pinicola* precursor,
   sonicating the *F. pinicola* precursor then centrifuging to obtain a *F. pinicola* extract;
   reacting the *F. pinicola* extract with titanium isopropoxide to form the TiO$_2$ nanoparticles; and
   isolating and drying the TiO$_2$ nanoparticles,
   wherein upon contacting the TiO$_2$ nanoparticles with colorectal cancer cells a cell viability of the colorectal cancer cells is reduced to 20% of a cell viability of a control group of colorectal cancer cells not contacted with the TiO$_2$ nanoparticles,
   wherein an amount of the TiO$_2$ nanoparticles in the contacting with the colorectal cancer cells is 0.5 µg per milliliter of a cell culture of the colorectal cancer cells,
   wherein upon contacting the TiO$_2$ nanoparticles with the colorectal cancer cells a cell nuclei of the colorectal cancer cells undergo nuclear condensation thereby killing a majority of the colorectal cancer cells,
   wherein the TiO$_2$ nanoparticles contain components of the *F. pinicola* as evident by Fourier transform infrared (FT-IR) spectroscopy absorption peaks at 1414 cm$^{-1}$, and 1000 cm$^{-1}$ corresponding to aliphatic C—N, and aromatic C=N bands, respectively,
   wherein the TiO$_2$ nanoparticles have a further FT-IR spectroscopy absorption peak at 3439 cm$^{-1}$ corresponding to —OH, and
   wherein the TiO$_2$ nanoparticles have a broadest dimension ranging from 80 to 120 nm.

2. The method of claim 1, wherein the TiO$_2$ nanoparticles are agglomerated.

3. The method of claim 1, wherein the TiO$_2$ nanoparticles are in a rutile phase and an anatase phase.

4. The method of claim 1, wherein in the reacting a ratio of the *F. pinicola* extract to the titanium isopropoxide by volume is 1:10, and
   wherein the titanium isopropoxide has a 1 millimolar concentration in water.

5. The method of claim 4, wherein the colorectal cancer cells are HCT-116 cells.

* * * * *